United States Patent
Smith et al.

(10) Patent No.: US 8,992,407 B2
(45) Date of Patent: Mar. 31, 2015

(54) BLOOD PUMP

(75) Inventors: William A. Smith, Lyndhurst, OH (US); Markus Lorenz, Karlsruhe (DE); David Dudzinski, Strongsville, OH (US); Hsiang Ming Chen, Latham, NY (US); Peter A. Chapman, Jr., East Schodack, NY (US); Charles J. Prisco, Saratoga Springs, NY (US); Nicholas G. Vitale, Albany, NY (US); Stephan Weber, Lyndhurst, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 13/470,539

(22) Filed: May 14, 2012

(65) Prior Publication Data

US 2012/0226097 A1    Sep. 6, 2012

Related U.S. Application Data

(62) Division of application No. 11/447,350, filed on Jun. 6, 2006, now Pat. No. 8,177,703.

(60) Provisional application No. 60/687,659, filed on Jun. 6, 2005.

(51) Int. Cl.
    *A61M 1/10* (2006.01)
(52) U.S. Cl.
    CPC ............. *A61M 1/101* (2013.01); *A61M 1/1031* (2014.02); *A61M 1/1015* (2014.02)
    USPC .................................. 600/16; 600/17; 600/18
(58) Field of Classification Search
    USPC ..................................................... 600/16–18
    See application file for complete search history.

(56) References Cited

U.S. PATENT DOCUMENTS

| 4,625,712 A | 12/1986 | Wampler |
| 4,704,121 A | 11/1987 | Moise |
| 4,779,614 A | 10/1988 | Moise |

(Continued)

FOREIGN PATENT DOCUMENTS

| DE | 299 21 352 U1 | 5/2001 |
| EP | 0 764 448 A2 | 3/1997 |

(Continued)

OTHER PUBLICATIONS

US 6,126,638, 10/2000, (withdrawn).

(Continued)

*Primary Examiner* — Carl H Layno
*Assistant Examiner* — Jon Eric C Morales
(74) *Attorney, Agent, or Firm* — Tarolli, Sundheim, Covell & Tummino LLP

(57) ABSTRACT

A blood pump (26) includes a stator assembly (122) that includes a motor stator, a fluid inlet (24), and a fluid outlet (26). A rotor assembly (120) includes a motor rotor (54) and an impeller (40) rotatable about an axis (44) to move fluid from the inlet (24) to the outlet (26). A permanent magnet radial bearing (100) supports the rotor assembly for rotation about the axis (44). The radial bearing (100) includes a permanent magnet radial bearing stator (106) fixed to the stator assembly (122) and a permanent magnet radial bearing rotor (108) fixed to the rotor assembly (120). The radial bearing (100) is configured such that the radial bearing stator magnets (106) and the radial bearing rotor magnets (108) are axially offset from each other when the pump is at rest.

59 Claims, 24 Drawing Sheets

(56) References Cited

U.S. PATENT DOCUMENTS

| | | |
|---|---|---|
| 4,817,586 A | 4/1989 | Wampler |
| 4,846,152 A | 7/1989 | Wampler et al. |
| 4,895,557 A | 1/1990 | Moise et al. |
| 4,906,229 A | 3/1990 | Wampler |
| 4,908,012 A | 3/1990 | Moise et al. |
| 4,957,504 A | 9/1990 | Chardack |
| 5,112,200 A | 5/1992 | Isaacson et al. |
| 5,211,546 A | 5/1993 | Isaacson et al. |
| 5,376,114 A | 12/1994 | Jarvik |
| 5,393,207 A | 2/1995 | Maher et al. |
| 5,507,629 A | 4/1996 | Jarvik |
| 5,588,812 A | 12/1996 | Taylor et al. |
| 5,613,935 A | 3/1997 | Jarvik |
| 5,692,882 A | 12/1997 | Bozeman, Jr. et al. |
| 5,707,218 A | 1/1998 | Maher et al. |
| 5,749,855 A | 5/1998 | Reitan |
| 5,755,784 A | 5/1998 | Jarvik |
| 5,776,190 A | 7/1998 | Jarvik |
| 5,824,070 A | 10/1998 | Jarvik |
| 5,840,070 A | 11/1998 | Wampler |
| 5,851,174 A * | 12/1998 | Jarvik et al. ............... 600/16 |
| 5,888,241 A | 3/1999 | Jarvik |
| 5,888,242 A | 3/1999 | Antaki et al. |
| 5,924,848 A | 7/1999 | Izraelev |
| 5,938,412 A | 8/1999 | Izraelev |
| 5,947,892 A | 9/1999 | Benkowski et al. |
| 5,951,263 A | 9/1999 | Taylor et al. |
| 5,957,672 A | 9/1999 | Aber |
| 5,964,694 A | 10/1999 | Siess et al. |
| 5,984,960 A | 11/1999 | Vitale |
| 6,015,272 A | 1/2000 | Antaki et al. |
| 6,018,208 A | 1/2000 | Maher et al. |
| 6,074,180 A | 6/2000 | Khanwilkar et al. |
| 6,093,001 A | 7/2000 | Burgreen et al. |
| 6,116,862 A | 9/2000 | Rau et al. |
| 6,123,659 A | 9/2000 | le Blanc et al. |
| 6,135,729 A | 10/2000 | Aber |
| 6,176,822 B1 | 1/2001 | Nix et al. |
| 6,183,412 B1 | 2/2001 | Benkowski et al. |
| 6,186,665 B1 | 2/2001 | Maher et al. |
| 6,190,409 B1 | 2/2001 | Vitale |
| 6,227,820 B1 | 5/2001 | Jarvik |
| 6,234,772 B1 | 5/2001 | Wampler et al. |
| 6,244,835 B1 | 6/2001 | Antaki et al. |
| 6,254,359 B1 | 7/2001 | Aber |
| 6,302,661 B1 | 10/2001 | Khanwilkar et al. |
| 6,344,022 B1 | 2/2002 | Jarvik |
| 6,368,083 B1 | 4/2002 | Wampler |
| 6,394,769 B1 | 5/2002 | Bearnson et al. |
| 6,447,265 B1 | 9/2002 | Antaki et al. |
| 6,447,266 B2 | 9/2002 | Antaki et al. |
| 6,527,521 B2 | 3/2003 | Noda |
| 6,527,699 B1 | 3/2003 | Goldowsky |
| 6,544,216 B1 | 4/2003 | Sammler et al. |
| 6,605,032 B2 | 8/2003 | Benkowski et al. |
| 6,652,447 B2 | 11/2003 | Benkowski et al. |
| 6,688,861 B2 | 2/2004 | Wampler |
| 6,716,189 B1 | 4/2004 | Jarvik et al. |
| 6,761,532 B2 | 7/2004 | Capone et al. |
| 7,011,620 B1 | 3/2006 | Siess |
| 8,177,703 B2 * | 5/2012 | Smith et al. ............... 600/16 |
| 2001/0009645 A1 | 7/2001 | Noda |
| 2001/0031210 A1 | 10/2001 | Antaki et al. |
| 2001/0037093 A1 | 11/2001 | Benkowski et al. |
| 2003/0021683 A1 | 1/2003 | Capone et al. |
| 2003/0023131 A1 | 1/2003 | Antaki |
| 2003/0069465 A1 | 4/2003 | Benkowski et al. |
| 2003/0144574 A1 | 7/2003 | Heilman et al. |
| 2003/0193252 A1 * | 10/2003 | Locke ............... 310/90.5 |
| 2003/0233144 A1 | 12/2003 | Antaki et al. |
| 2004/0191116 A1 | 9/2004 | Jarvik et al. |
| 2004/0215050 A1 | 10/2004 | Morello |
| 2004/0228724 A1 | 11/2004 | Capone et al. |
| 2004/0241019 A1 | 12/2004 | Goldowsky |

FOREIGN PATENT DOCUMENTS

| | | |
|---|---|---|
| EP | 1 481 698 A2 | 12/2004 |
| WO | WO 9737697 A1 | 10/1997 |
| WO | WO 9737698 A1 | 10/1997 |
| WO | WO 0033445 A1 | 6/2000 |
| WO | WO 0215963 A1 | 2/2002 |
| WO | WO 0241935 A1 | 5/2002 |
| WO | WO 03075981 A1 | 9/2003 |
| WO | WO 2004098677 A1 | 11/2004 |
| WO | WO 2004101029 A1 | 11/2004 |

OTHER PUBLICATIONS http://www.fosmiltech.com/pages/minicath.html (1 pg.) dated Aug. 28, 2003.

http://www.fosmiltech.com/pages/newcurrent.html (2 pgs.) dated Aug. 28, 2003.

Chen et al., "A Self-Sufficient Magnetic Bearing", 6th Int'l Symp. on Magnetic Suspension Technology, Oct. 7-11, 2001, Turin, Italy.

Chen et al. "Development of Magnetically Levitated Blood Pumps", 6th Int'l Symp. on Magnetic Suspension Technology, Oct. 7-11, 2001, Turin, Italy.

Duncan et al., "The PediPump: A New Ventricular Assist Device for Children", 12th Congress of the Int'l Society for Rotary Blood Pumps, Oct. 7-10, 204, Cleveland, OH, USA.

Wampler et al., "A Sealless Centrifugal Blood Pump with Passive Magnetic and Hydrodynamic Bearings", Artificial Organs 1999: 23(8) 780-784.

Macris et al., In Vivo Eval. of an Intravent. Electric Axial Flow Pump for Left Ventricular Assis., ASAIO Jour. 40 Jul.-Sep. 1994, No. 3 Hagerstown, MD, US, XP-000498262.

* cited by examiner

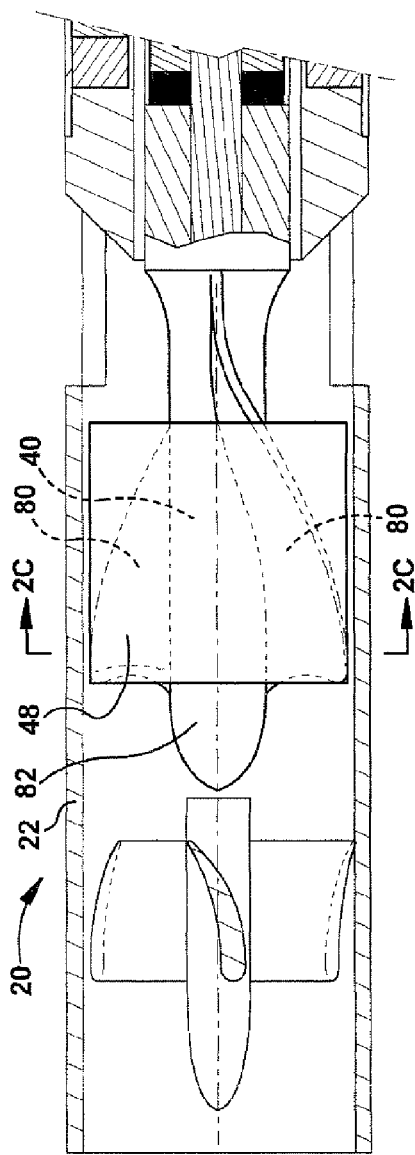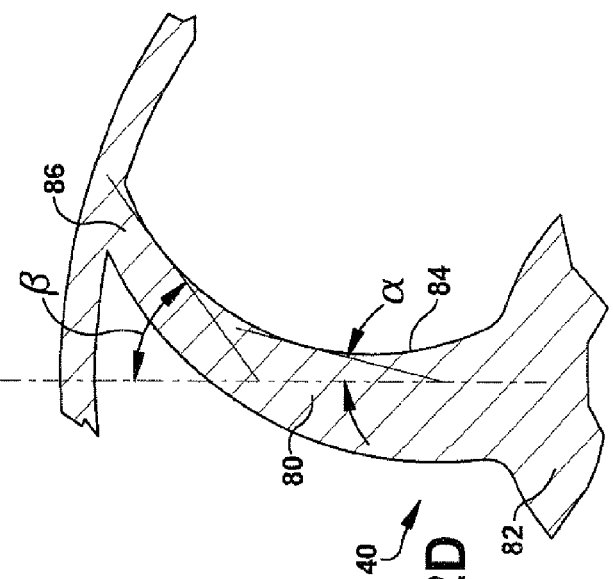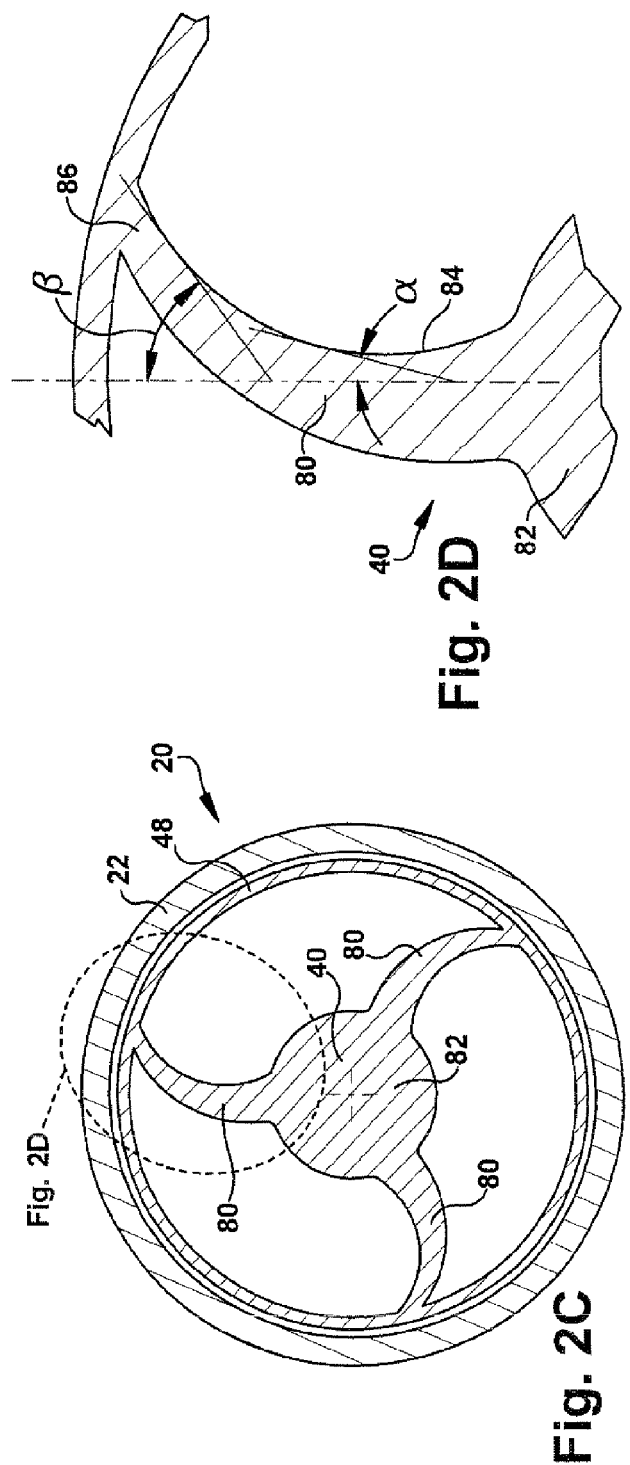

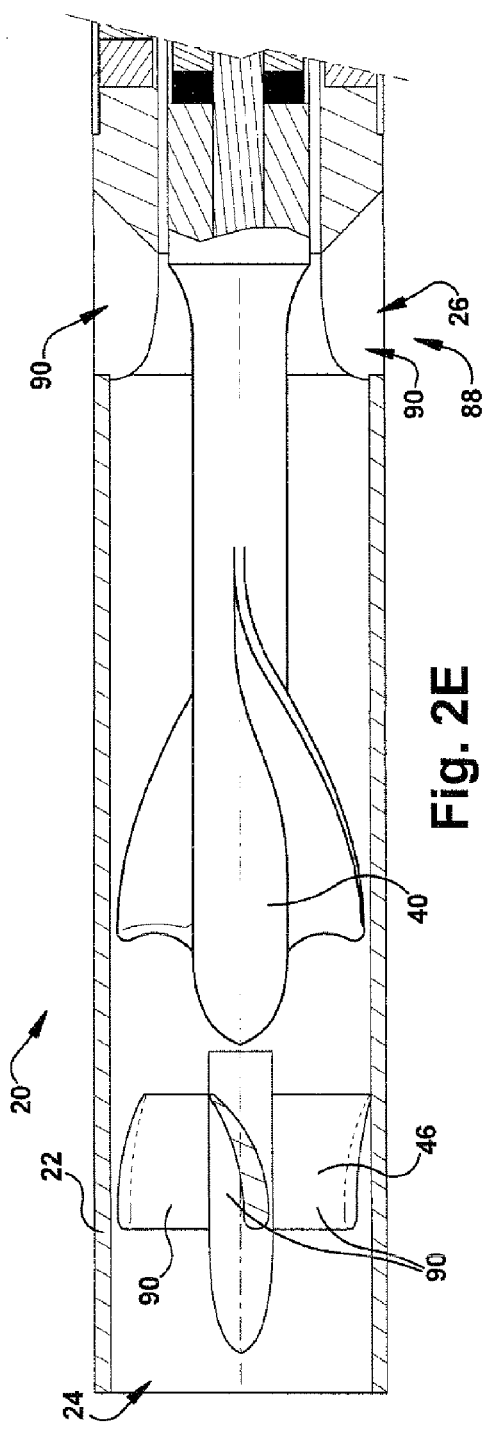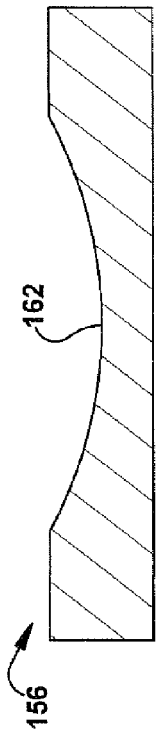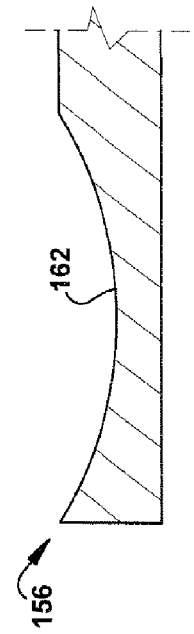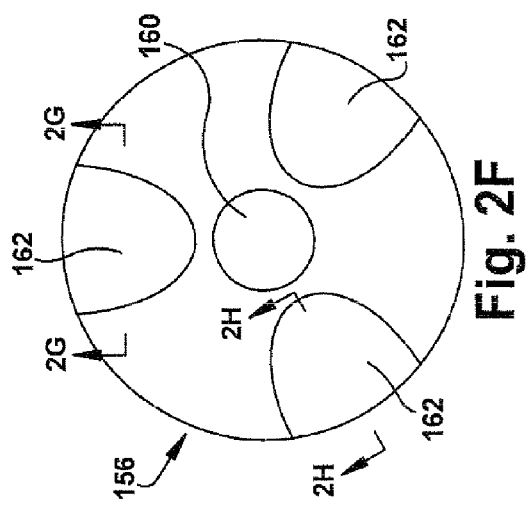

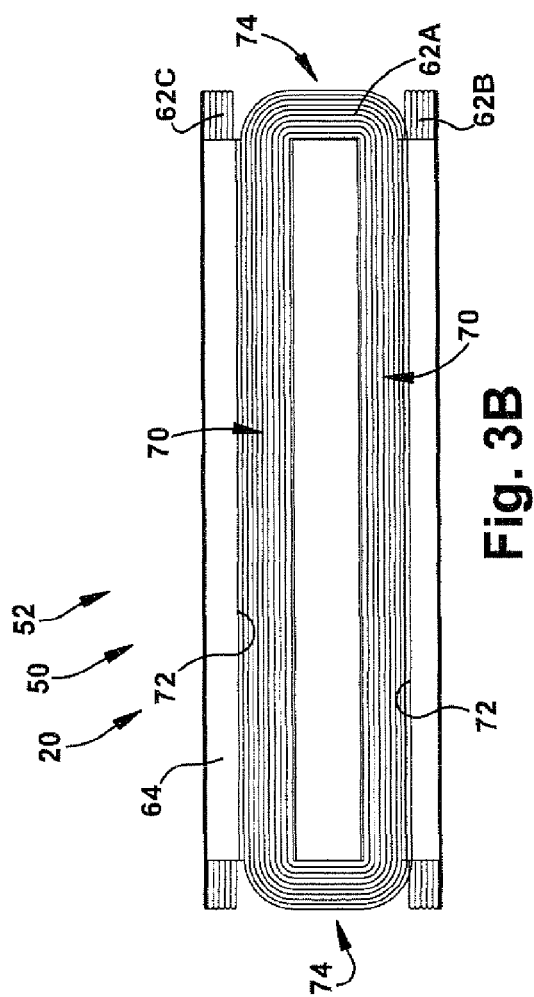
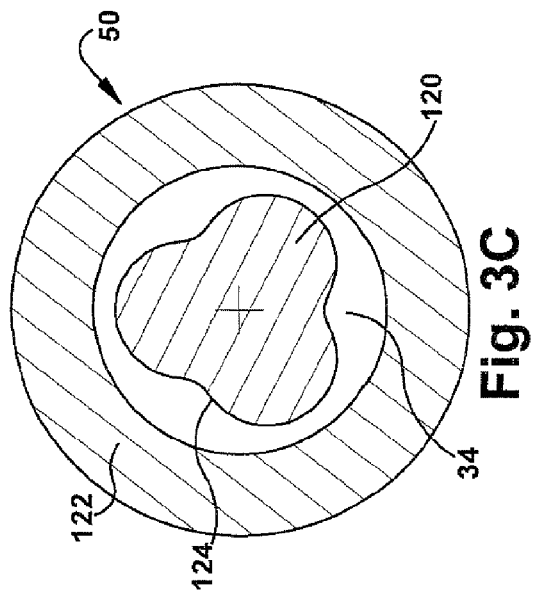
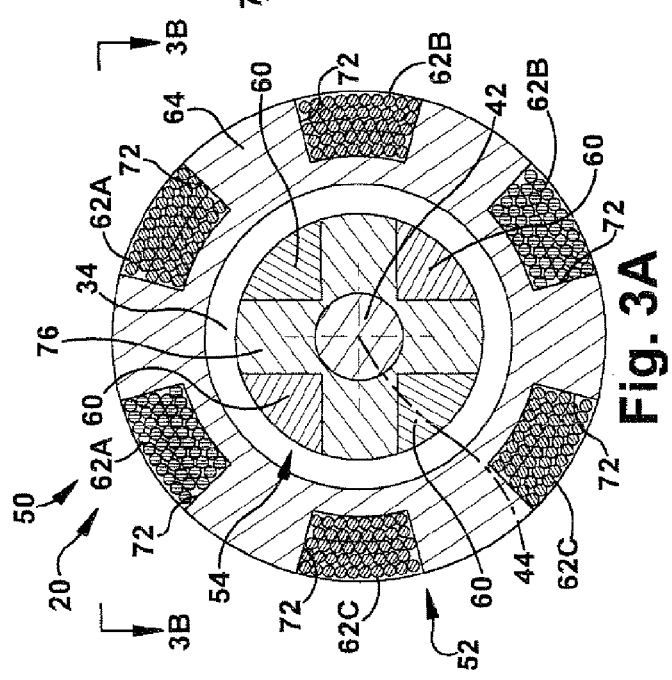
Fig. 3A
Fig. 3B
Fig. 3C

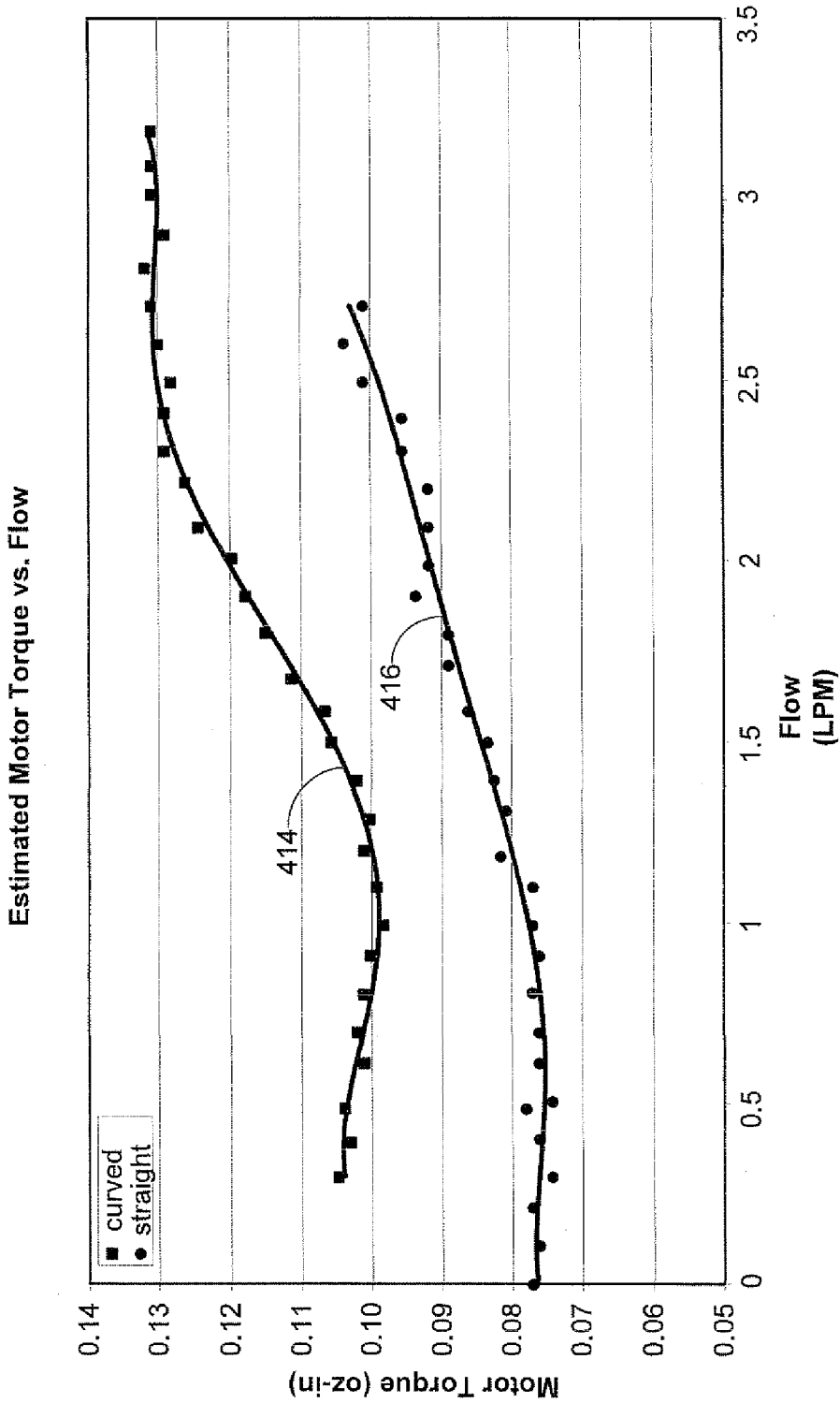

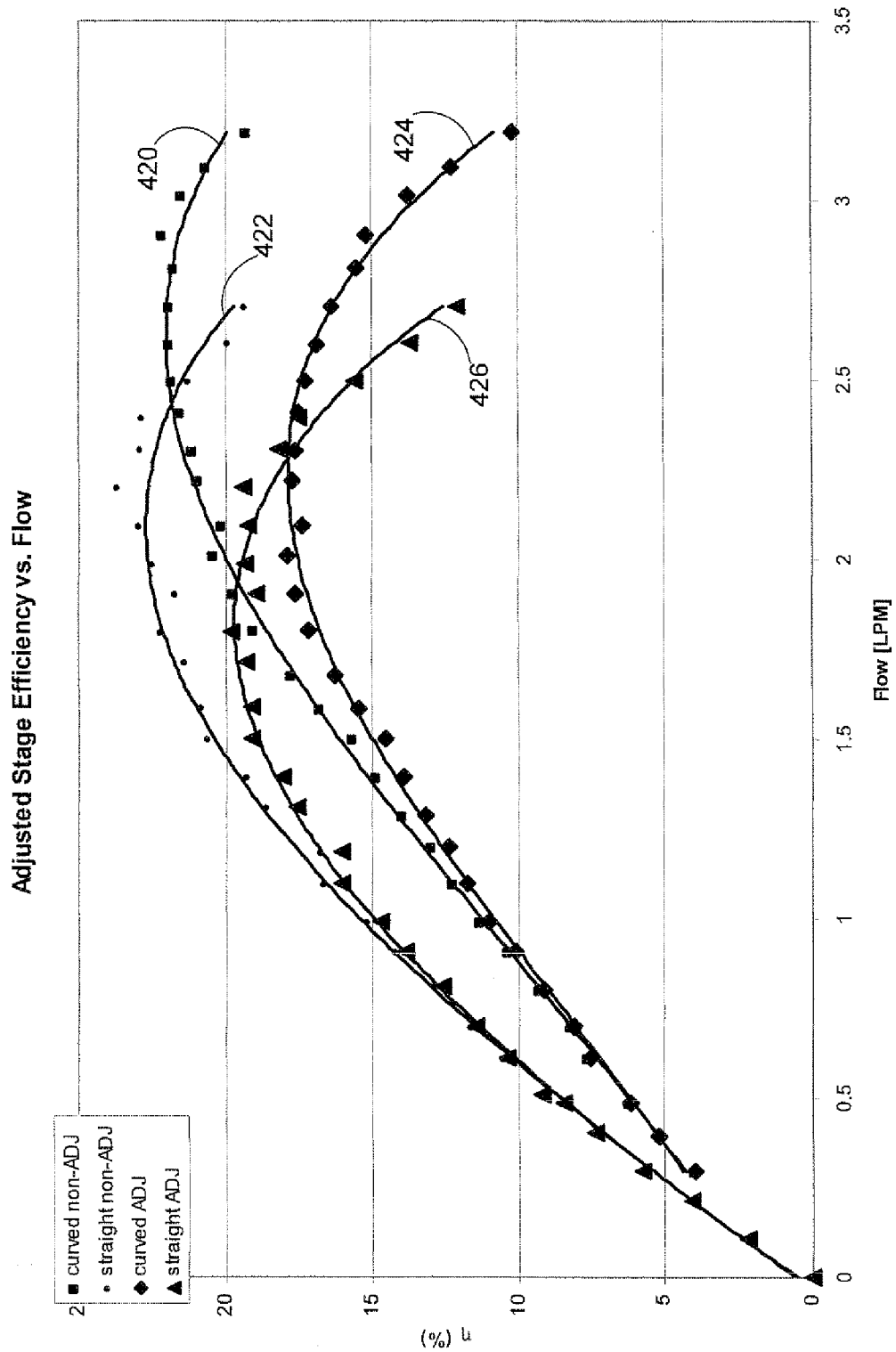

BLOOD PUMP

RELATED APPLICATIONS

This application is a divisional of U.S. patent application Ser. No. 11/447,350 filed on Jun. 6, 2006, which issued on May 15, 2012 as U.S. Pat. No. 8,177,703 B2, and which claims the benefit of U.S. Provisional Application No. U.S. 60/687,659, filed Jun. 6, 2005.

GOVERNMENT RIGHTS

The invention described in this application was supported, at least in part, by United Stated Government Contract Nos. HHSN268200448188C and HL67487 with the National Heart, Lung and Blood Institute and the National Institutes of Health.

TECHNICAL FIELD

The present invention relates to a blood pump. More particularly, the present invention relates to an implantable intravascular or intracorporeal extravascular blood pump that may be used as a ventricular assist device.

BACKGROUND OF THE INVENTION

In the field of adult cardiac surgery, ventricular assist devices (VADs) are now reaching high levels of success, with the bridge to transplant cases numbering in the thousands. An appreciation has developed that many adult patients can be successfully treated with much lower levels of device flow than were once considered necessary. Placement of the pumping device, in terms of both size and delivery method, are frequently more critical issues than maximum possible pump output. The recent advances in adult blood pumping now enable pediatric mechanical circulatory support not previously practical. While the pediatric patient numbers are much smaller, the potential in recovered patient-years is relatively high. Given adequate support, the likelihood of long-term recovery for pediatric patients is very high.

Extracorporeal membrane oxygenation (ECMO) is the most common approach to pediatric cardiac salvage today, regardless of the presence or absence of pulmonary failure. This can be attributed to both a lack of good pediatric assist device systems, and the extensive pediatric experience utilizing ECMO for the treatment of respiratory failure. This is unfortunate because many of the bleeding, thromboembolic, and immune related complications can be attributed to the large surface areas of the oxygenators and the required anticoagulation, as well as high potential for clot formation in flow paths and complement activation by the foreign surfaces. In addition, ECMO systems restrict patient mobility and are suitable only for short-term support.

While the use of VADs for pediatric circulatory support has been shown to result in significantly fewer long-term complications compared to ECMO support, the development of pediatric VADs remains substantially behind that of adult systems. To this point, VAD experience has been limited primarily to centrifugal pump based systems, and pulsatile systems that are limited to a paracorporeal configuration. To accommodate the entire size range of pediatric patients while maintaining internal pump washout, a large number of different volume pumps must be maintained in most product lines. Due to size constraints, none of these systems are designed to be fully implantable for the majority of children.

Children who require mechanical circulatory support after failing routine medical management represent the most critically ill subset of an already challenging patient population. As in adult patients, pediatric patients can now benefit from some of the exciting advances that are occurring in the field of mechanical support for cardiorespiratory failure. The pediatric population has not, however, received the same attention in terms of product development, as has the adult population. For example, currently there are no pulsatile or implantable VADs available for infants and small children in the United States, while at many centers ECMO remains their only available form of mechanical circulatory support. In addition, unique features of circulatory failure in children limit the applicability of advances made in device development for adults. Accordingly, there is a need for focused research and development leading to devices that provide circulatory support for children with full consideration of the anatomic and physiologic requirements unique to pediatrics.

One consideration in the design and development of circulatory support systems for children is related to patient size. It is desirable for the pediatric mechanical circulatory support device to provide support across a large range of patients sizes—from newborns to young adults and through adulthood. Paracorporeal VADs that are currently available for children in Europe rely on a number of pump sizes to cover the range of patients encountered in pediatric practice, which substantially increases both development and patient costs. Also, paracorporeal systems result in major skin penetrations, and expose the circulatory flow path to risk of mechanical damage. Beyond implications for the pump itself, size considerations exist for all aspects of device design for children including cannulas, energy sources and control mechanisms.

In addition to considerations of patient size, the design of circulatory support systems for children takes into account other physiologic considerations unique to pediatrics. Children, especially newborns, may be more prone to complications related to anticoagulation. Higher doses of anticoagulation medications required for ECMO may make intracranial hemorrhage more common resulting in poorer neurologic outcomes compared to VAD supported children. Therefore, it is desirable that the pediatric circulatory support system operates with minimal or no anticoagulation. Children are vulnerable to infectious complications and, as a result, a large percentage of children who die during mechanical circulatory support are those who succumb to infection. A large percentage of children require the urgent institution of support to treat cardiac arrest after cardiac surgery or in the setting of acute myocarditis. Therefore, it is desirable that designs for the circulatory support system allow for rapid deployment, which has been shown to substantially improve outcomes for children requiring support for cardiac arrest.

Newborns often manifest an exaggerated systemic inflammatory response after cardiopulmonary bypass, which frequently evolves into multi-system organ failure during prolonged ECMO or VAD support. Therefore, it is desirable that the circulatory support system has maximal biocompatibility to help prevent activation of systemic inflammatory cascades by providing minimal trauma to blood elements and possibly by providing pulsatile perfusion.

SUMMARY OF THE INVENTION

The invention relates to a blood pump that includes a stator assembly that includes a motor stator, a fluid inlet, and a fluid outlet. A rotor assembly includes a motor rotor and an impeller rotatable about an axis to move fluid from the inlet to the outlet. A permanent magnet radial bearing supports the rotor assembly for rotation about the axis. The radial bearing includes a permanent magnet radial bearing stator fixed to the stator assembly and a permanent magnet radial bearing rotor fixed to the rotor assembly. The radial bearing is configured such that the radial bearing stator magnets and the radial bearing rotor magnets are axially offset from each other when the pump is at rest.

The invention also relates to a blood pump that includes a housing that includes an elongated tubular side wall that extends along a central axis of the blood pump. The housing has a fluid inlet and a fluid outlet. The fluid outlet includes at least one opening in the side wall. An impeller is positioned in the housing for rotation about the axis. At least a portion of the impeller is positioned between the fluid inlet and the fluid outlet. A motor imparts rotation of the impeller about the axis. The motor includes a stator fixed to the housing, a rotor coupled to the impeller, and a permanent magnet radial bearing for supporting the rotor for rotation about the axis. The radial bearing includes a permanent magnet radial bearing stator and a permanent magnet radial bearing rotor. The radial bearing is configured such that the radial bearing stator magnets and the radial bearing rotor magnets are axially offset from each other when the pump is at rest.

BRIEF DESCRIPTION OF THE DRAWINGS

The foregoing and other features of the present invention will become apparent to those skilled in the art to which the present invention relates upon reading the following description with reference to the accompanying drawings, in which:

FIGS. 2B and 2C are sectional views illustrating an alternative configuration of the blood pump of FIG. 2A;

FIG. 2D is a magnified view of a portion of the blood pump of FIG. 2A;

FIG. 2E is a sectional view illustrating an alternative configuration of the blood pump of FIG. 2A;

FIGS. 2F-H are a magnified views of a portion of the blood pump of FIG. 2A;

FIG. 3A is a sectional view of a portion of the blood pump of FIG. 2A;

FIG. 3B is a top view of a portion of the blood pump of FIG. 2A;

FIG. 3C is a sectional view illustrating an alternative configuration of the blood pump of FIG. 2A;

FIGS. 11A-11F are charts illustrating the effects of an inflow stator configuration of the present invention.

DESCRIPTION OF EMBODIMENTS

The present invention relates to a blood pump. In the embodiments illustrated herein, the blood pump is depicted as an implantable blood pump for use as a ventricular assist device (VAD). The pump of the present invention provides an implantable adult or pediatric ventricular assist device that may be used for short to long-term applications. Through flexible implant approaches, the pump is adaptable to patient size and to the special anatomic features that may be encountered when treating congenital heart disease. The pump may be implemented as a Right Ventricular Assist Device (RVAD), a Left Ventricular Assist Device (LVAD), or a Bi-Ventricular Assist Device (BVAD), with intravascular and intracorporeal extravascular implant options for each implementation. This flexibility provides the surgeon great freedom in matching the procedure with the range of patient size and anatomical variations found in congenital heart disease.

Figure 1:
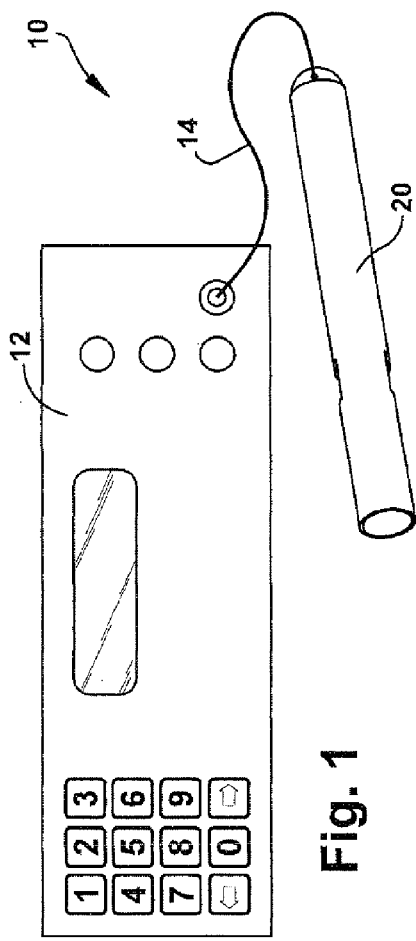
FIG. 1 is a perspective view of a blood pumping system according to a first embodiment of the present invention.

FIG. 1 illustrates an example configuration of a system 10 that includes a mixed flow pump 20 of the present invention. As used herein the term "mixed flow pump" is meant to describe a pump in which, as fluid flows through the impeller, the fluid has significant velocity imparted in both axial and radial directions.

The pump system 10 includes an electronic control unit 12 (ECU) that is operatively connected to the pump 20 by one or more cables 14. The ECU 12 is operative to supply pump motor control voltage, such as pulse width modulated (PWM) motor control voltages, to the pump 20 via the cable 14 in a known manner. The ECU 12 is also operative to receive feedback or other I/O from the pump via the cable 14. Those skilled in the art will appreciate that the system 10 may be adapted for alternative power/control schemes. For example, the system 10 may be adapted such that the ECU 12 is a portable battery powered unit for an ambulatory patient. As another example, the system 10 may be adapted such that the ECU 12 is an implantable battery powered unit that may be recharged either by lead wires or by transcutaneous energy transmission. As a further example, the pump 20 and ECU 12 may be adapted for telemetric transmission of data in order to eliminate one or more control wires penetrating the patient's skin.

Figure 2A:
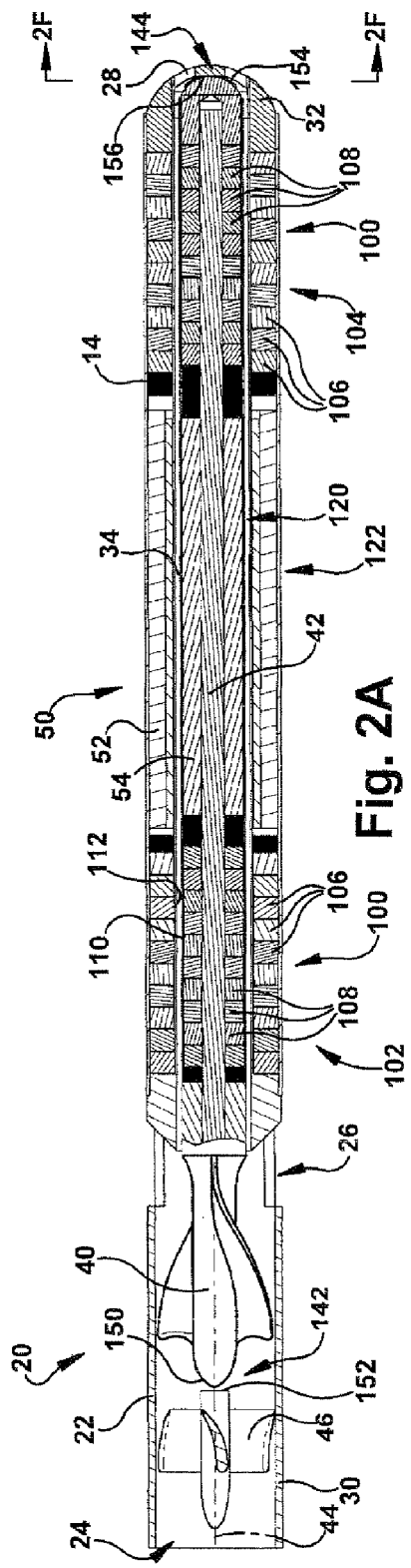
FIG. 2A is a sectional view of a blood pump of the blood pumping system of FIG. 1.

Referring to FIG. 2A, the pump 20 includes a housing 22 with an inlet port 24, one or more radial outlet ports 26, and a wash flow port 28. The housing 22 has an open first end 30 that forms the inlet port 24 and a closed opposite end 32. The pump 20 includes an impeller 40 that is supported on a shaft 42 that is rotatable about an axis 44 of the pump. An inflow stator 46 is centered on the axis 44 and is positioned in the inlet port 24 adjacent the impeller 40. The impeller 40, shaft 42, and inflow stator 46 are constructed of non-ferrous materials, such as stainless steel, titanium, ceramics, polymeric materials, composite materials, or a combination of these materials. In one particular embodiment, the shaft 42 may be constructed of a Zirconia material.

The pump 20 includes a motor portion 50 that is adapted to impart rotation of the shaft 42 and impeller 40. The motor 50 may be any suitable electric motor, such as a multi-phase motor in which each phase is excited via pulse-width modulated voltage provided by the control unit 12. The motor 50 includes a stator 52 supported by the housing 22 and a rotor 54 supported on the shaft 42. The stator 52 comprises one or more poles or windings, such as copper wire windings, wound on a stator core. The rotor 54 comprises one or more permanent magnets, such as Neodymium Iron Boron (Nd-FeB) magnets, arranged in a cylindrical fashion on the shaft 42 and extending coaxially with the shaft. The control unit 12 is operative to supply motor control voltage to the motor stator 52 to excite the windings and induce rotation of the rotor 54.

Referring to FIGS. 3A and 3B, in one particular embodiment of the pump 20, the motor 50 has a four (4) pole, three (3) coil configuration. As shown in FIG. 3A, the rotor 54 includes a back iron 76 having a cross-shaped cross section that defines recesses having perpendicularly oriented rectangular surfaces in which the permanent magnets 60 are received and supported. In the four pole configuration, the rotor 54 includes four permanent magnets 60 spaced equally about the shaft 42. As shown in FIG. 3A, the rotor 54 has an overall cylindrical configuration.

Referring to FIGS. 3A and 3B, the stator 52 includes a stator core 64 and three coils 62, identified individually at 62A, 62B, and 62C, spaced equally about the stator core 64. The stator core 64 is configured such that the three-phase coils 62 have an elongated configuration with straight sections 70 that extend axially along slots 72 in the stator core and end turns 74 at opposite ends of the slots. In this configuration, the end turns 74 of different phase coils 62 do not wrap around or pass over end turns of other phases.

Referring to FIG. 3A, the stator 52 is an ironless stator, i.e., the stator core 64 is constructed of a low magnetic permeability, non-ferrous material, such as stainless steel, titanium, copper, ceramics, polymeric materials, composite materials, or a combination of these materials. The ironless stator configuration of the motor 50 helps minimize side pull in the motor 50, i.e., the magnetic attraction between the rotor 54 and stator 52, which may help reduce the size and stiffness of magnetic radial bearings required to overcome side pull in the motor 50.

Referring to FIG. 2A, the pump 20 also includes radial bearings 100 that help support the shaft 42 and impeller 40 for rotation about the axis 44. In the illustrated embodiment, the radial bearings 100 include a front radial bearing 102 and a rear radial bearing 104 positioned adjacent opposite ends of the motor 50. The radial bearings 100 are permanent magnet bearings that utilize permanent magnets, such as NdFeB magnets. Each radial bearing 100 comprises a plurality of ring-shaped stator magnets 106 and a plurality of ring-shaped rotor magnets 108. In the embodiment of FIG. 2A, the front radial bearing 102 and rear radial bearing 104 each include ten stator magnets 106 and ten rotor magnets 108. The radial bearings 100 could have any desired number of stator and rotor magnets. The implementation of the permanent magnet radial bearings 100 helps eliminate the need for a seal, as is required with conventional mechanical radial bearings.

From the description thus far, it will be appreciated that the pump 20 includes a rotor assembly 120 and a stator assembly 122. The rotor assembly 120 includes the impeller 40, shaft 42, motor magnets 60, back iron 76, radial bearing rotor magnets 108 and any encasing material used to coat or otherwise protect the pump. The stator assembly 122 includes the housing 22, inflow stator 46, motor stator core 64, motor stator windings 62, and the radial bearing stator magnets 106 and any encasing material. The motor 50 imparts rotation of the rotor assembly 120 relative to the stator assembly 122.

The radial bearings 100 support the rotor assembly 120 for rotation relative to the stator assembly 122.

A radial motor gap 34 of the motor portion 50 is defined between the rotor assembly 120 and stator assembly 122. As shown in FIG. 3A, the motor gap 34 has a an annular configuration defined by the spaced cylindrical surfaces of the rotor assembly 120 and stator assembly 122. As shown in FIG. 3C, however, in an alternative configuration of the motor portion 50, the surface of the rotor assembly 120 that helps define the motor gap 34 may comprise a portion 124 may have a non-cylindrical configuration. The non-cylindrical, curved configuration of the surface 124 can help contribute to the fluid dynamic stability of the flow pattern in the motor gap 34.

The pump 20 also includes mechanical axial or thrust bearings 140. The axial bearings 140 include front and rear axial bearings 142 and 144, respectively, positioned at opposite ends of the rotor assembly 120, that help support the rotor assembly 120 for rotation relative to the stator assembly 122. The front axial bearing 142 comprises a convex rounded terminal end portion 150 of the impeller 40 and a mating surface 152 of the inlet stator 46. The surface 152 acts as a front stop that helps control or limit forward axial movement and the axial position of the rotor assembly 120 relative to the stator assembly 122. The rear axial bearing 142 comprises a convex rounded terminal end portion 154 of the rotor assembly 120 and a mating surface 156 on the stator assembly 122. The surface 156 acts as a rear stop that helps control or limit rearward axial movement and the axial position of the rotor assembly 120 relative to the stator assembly 122.

Mating or engaging surfaces of the front and rear axial bearings 142 and 144 may be coated or constructed with materials that produce low friction, such as Teflon®, diamond-like carbon coatings, ceramics, titanium, and diamond coated titanium. In one particular example, the axial bearing surfaces of the rotor assembly 120, i.e., the portions 150 and 154, are coated or otherwise formed with a chrome-cobalt material, and the axial bearing surfaces of the stator assembly 122, i.e., the portions 152 and 156, are coated or otherwise formed of a ceramic material, which has been shown to provide performance superior to that of conventional bearing surfaces, such as ceramic-on-ceramic bearing surfaces or diamond-like carbon-on-diamond-like carbon bearing surfaces. In another example, the axial bearing surfaces of the rotor assembly 120, i.e., the portions 150 and 154, are coated or otherwise formed with a synthetic jewel material (e.g., synthetic ruby, sapphire, or diamond materials), and the axial bearing surfaces of the stator assembly 122, i.e., the portions 152 and 156, are coated or otherwise formed of a ceramic material.

The pump 20 is constructed such that parts that come into contact with blood are made of a biocompatible material. The motor magnets 60, back iron 76, and radial bearing rotor magnets 108 are encased or otherwise covered or coated on the shaft 42 by a biocompatible material 110. Examples of such materials are titanium and stainless steel. The motor stator 52, i.e., the stator core 64 and windings 62, and the radial bearing stator magnets 106 are also encased or otherwise covered or coated on the housing 22 by a biocompatible material 112. Further, the impeller 40 and inflow stator 46 are constructed, encased, or otherwise covered or coated with a biocompatible material. For example, the impeller 40 and inflow stator 46 may be constructed of titanium or molded from a biocompatible polymeric material.

Referring to FIG. 2A, during operation, blood enters the pump 20 axially at the inlet 24, is turned in the impeller 40, exits the pump at an intermediate angle through the outlets 26, and flows along the outside diameter of the pump. The flow through the outlet 26 is thus a mixed flow having both axial and radial components. The primary flow of the pump 20 is thus placed outside the pump 20 instead of through the motor gap 34, which allows the motor gap to be sized without having to consider primary flow requirements through motor gap. This allows the pump 20 to have a small package size while maintaining a motor gap sufficiently large to provide low blood shear.

Also, during operation of the pump 20, some blood flows into the motor gap 34 through the wash flow port 28. This wash flow washes exposed parts of the pump 20/motor 50 to help prevent deposition and also cools the motor gap 34 before returning to the impeller 40 and being pumped through the outlets 26. The wash flow direction is from rear to front, i.e., from the wash flow port 28 to the impeller 40, due to the pressure rise of the pump. The wash flow may be directed to a midpoint on the impeller 40 to help improve wash flow.

Figure 11A:
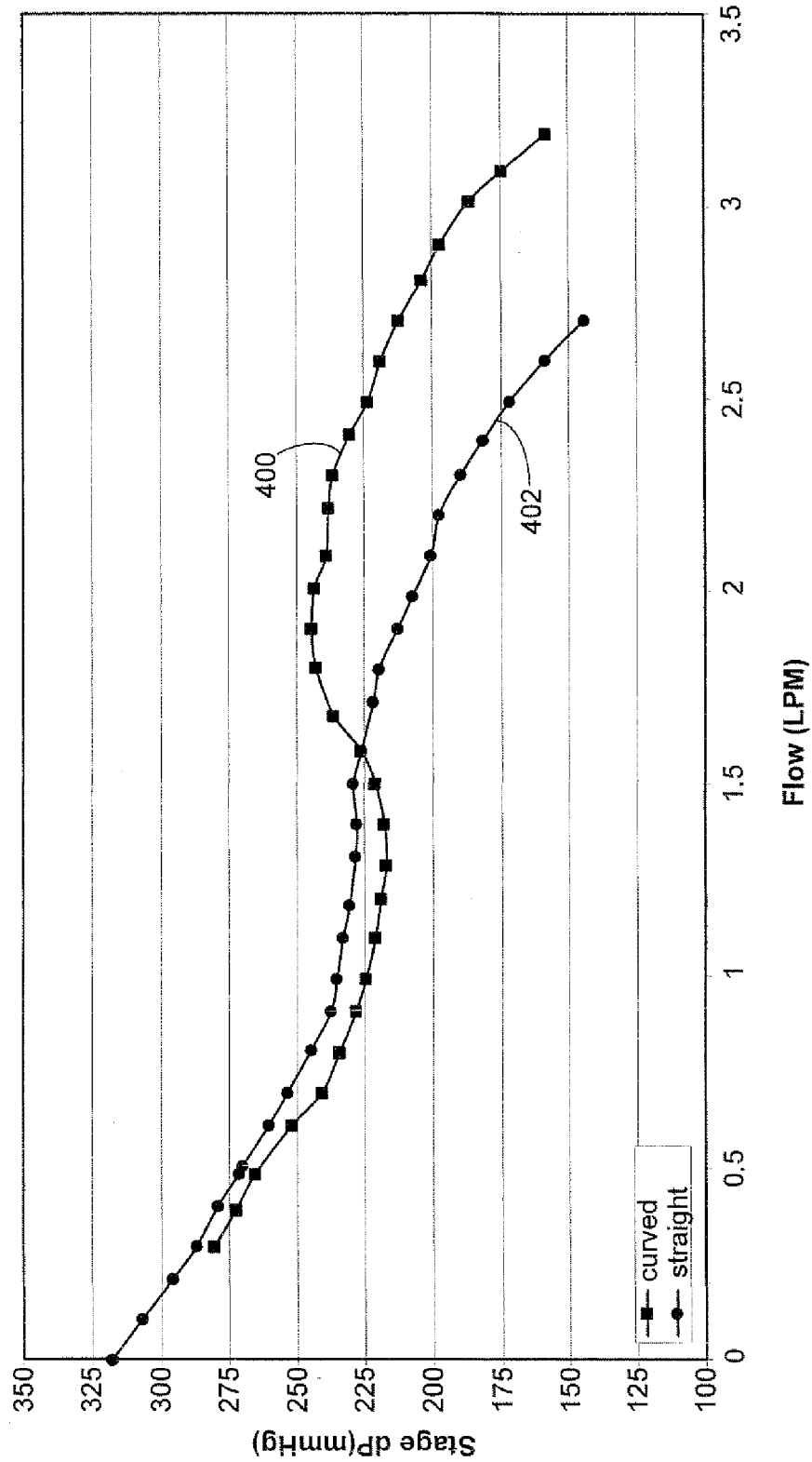

The inlet stator 46 may have a vane configuration with a curvature reversed from that of the vanes of the impeller 40. This helps produce a reverse pre-swirl in the inflow blood, i.e., a swirl in the blood in a direction opposite the rotation of the impeller 40. Testing has shown that a pre-swirl created in the inflow blood by the inlet stator 46 helps improve the performance characteristics of the pump 20. FIGS. 11A 11F illustrate selected performance characteristics for a pump configured with the reversed curvature inlet stator 46 of the present invention versus a pump configured with a conventional non-curved or straight inlet stator.

In the tests used to gather the data shown in FIGS. 11A-11F, the test pump was operated at a nominal speed of 60,000 RPM. To perform the tests, the pump was operated at this nominal speed pumping a fluid having a composition that simulates blood. An outlet conduit connected to the pump was clamped to restrict outlet flow from the pump. The pump was then operated at the nominal speed, the clamp was systematically opened to predefined positions, and data readings were taken at each position to gather the data points in FIGS. 11A-11F. Thus, in FIGS. 11A-11F, data point pairs for the reverse curved and straight inlet vane configurations correspond to these predefined clamp positions. For example, in FIGS. 11A-11F, the data points on the far right ends of the curves correspond to the last of the predefined clamp positions. Going backward or to the left in FIGS. 11A-11F, the next-to-last data points correspond to the next-to-last predefined clamp position, and so on. For purposes of this description, a flow of three (3) liters per minute (LPM) at a 90 mmHg pressure rise across the pump are used as nominal or baseline performance characteristics for purposes of comparing the different inlet stator configurations.

FIG. 11A illustrates stage pressure rise versus flow characteristics for a pump fit with a curved inlet stator 46 at the line indicated at 400 versus a pump fit with a conventional or non-curved inlet stator at the line indicated at 402. The stage pressure rise is the inlet pressure measured immediately before the stator vane within the shroud diameter, subtracted from the outlet pressure measured in the outlet chamber representative of the aorta.

Figure 11B:
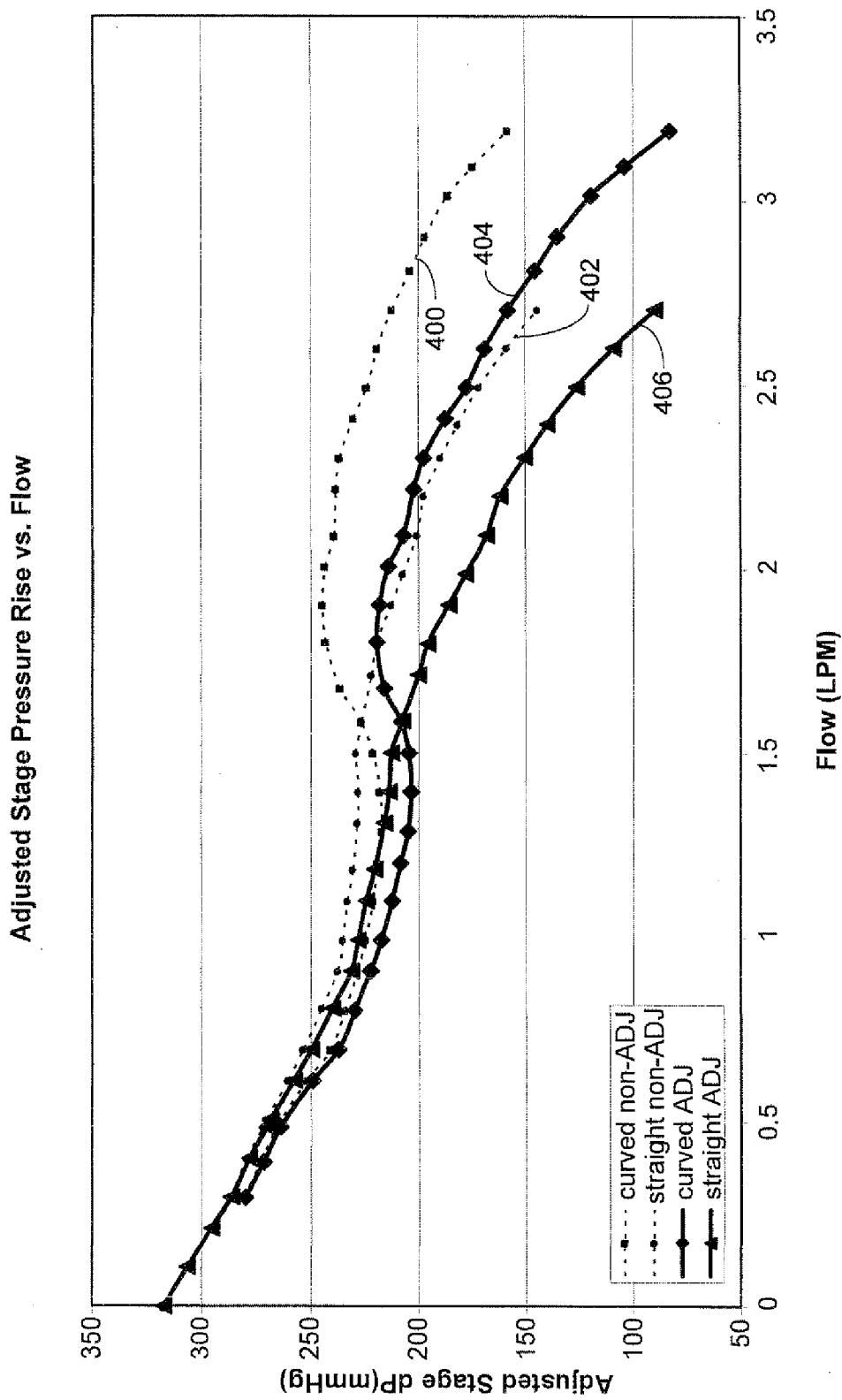

FIG. 11B illustrates adjusted stage pressure rise versus flow characteristics for a pump fit with a curved inlet stator 46 at the line indicated at 404 versus a pump fit with a conventional or non-curved inlet stator at the line indicated at 406. For comparison, the non-adjusted values from FIG. 11A are included in FIG. 11B at 400 and 402. The adjusted stage pressure rise is the estimated pressure just outside the pump inlet subtracted from the outlet pressure measured in the outlet chamber representative of the aorta. The estimated pressure outside the pump inlet is calculated by subtracting reentrant flow losses due to pump insertion into a larger cavity from the measured inlet pressure.

Referring to FIGS. 11A and 11B, it can be seen that, other conditions being equal, the pump outfitted with the reversed curved vane inlet stator is capable of achieving the 3 LPM flow at a pressure rise far in excess of the nominal value of 90 mmHg. In comparison, in the same conditions, the straight vane inlet stator falls to meet the 3 LPM flow.

Figure 11C:
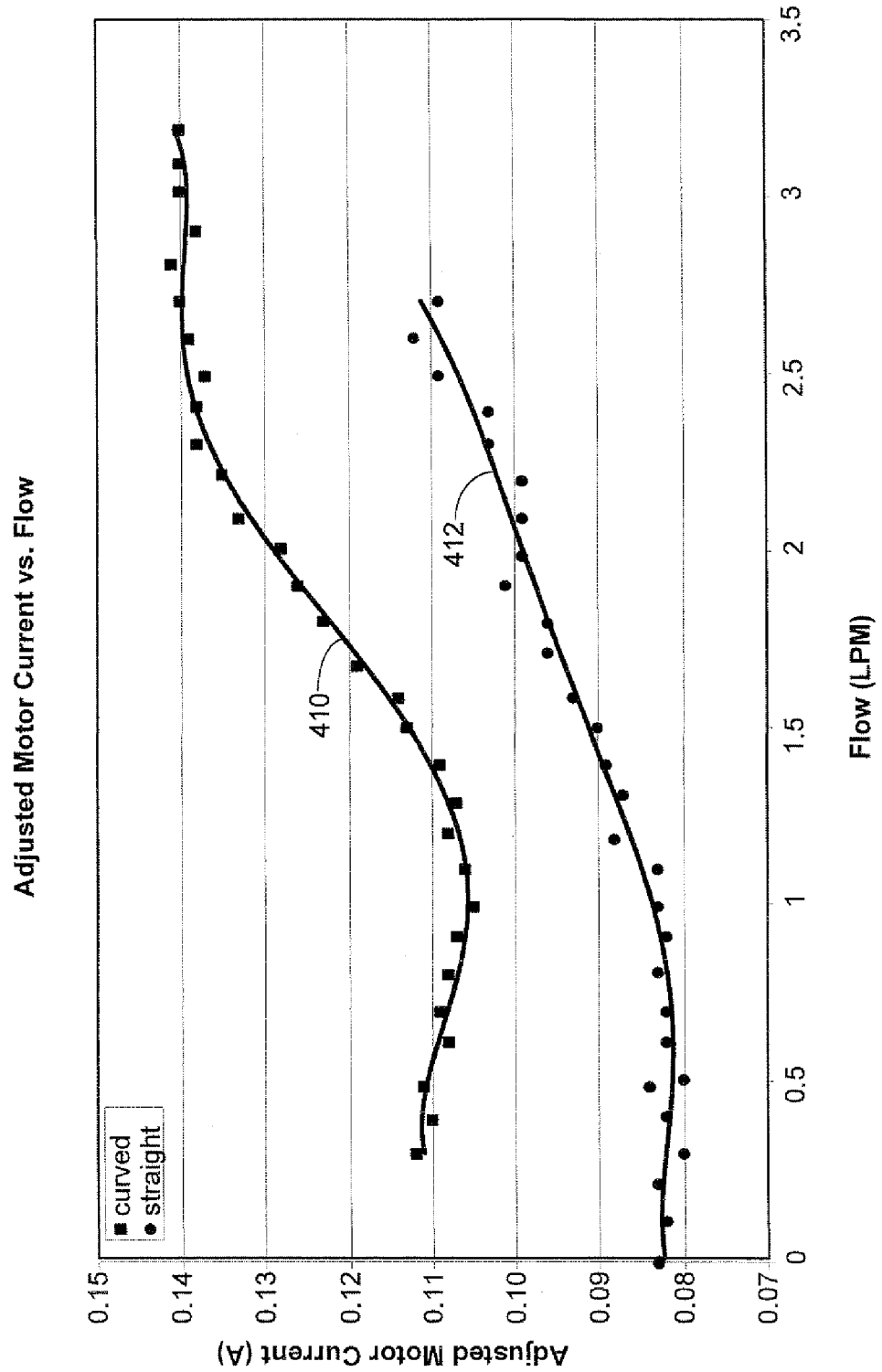

FIG. 11C illustrates adjusted motor current versus flow characteristics for a pump fit with a curved inlet stator 46 at the line indicated at 410 versus a pump fit with a conventional or non-curved inlet stator at the line indicated at 412. The adjusted motor current is the free running speed current subtracted from the recorded motor current.

FIG. 11D illustrates estimated motor torque versus flow characteristics for a pump fit with a curved inlet stator 46 at the line indicated at 414 versus a pump fit with a conventional or non-curved inlet stator at the line indicated at 416. The adjusted motor torque is the adjusted motor power divided by pump speed. Adjusted motor power is the adjusted motor current multiplied by the supply voltage.

Figure 11E:
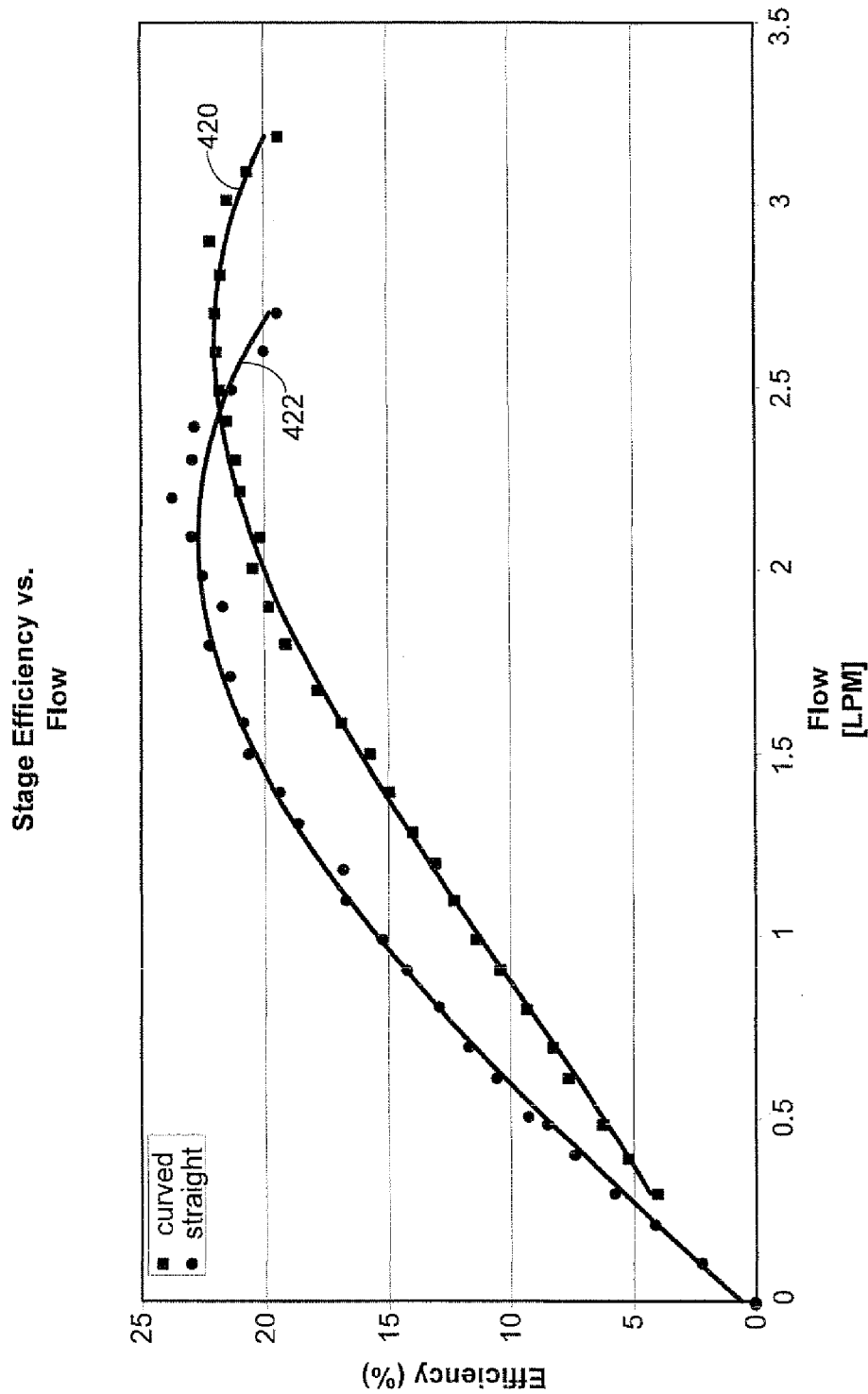

FIG. 11E illustrates stage efficiency versus flow characteristics for a pump fit with a curved inlet stator 46 at the line indicated at 420 versus a pump fit with a conventional or non-curved inlet stator at the line indicated at 422. The stage efficiency is the non-adjusted hydraulic power divided by the adjusted motor power.

FIG. 11F illustrates adjusted stage efficiency versus flow characteristics for a pump fit with a curved inlet stator 46 at the line indicated at 424 versus a pump fit with a conventional or non-curved inlet stator at the line indicated at 426. For comparison, the non-adjusted values from FIG. 11E are included in FIGS. 11B at 420 and 422. The adjusted stage efficiency is the adjusted hydraulic power divided by the adjusted motor power. The adjusted hydraulic power is the adjusted stage differential pressure rise multiplied by flow. The adjusted stage differential pressure is determined by subtracting reentrant flow losses due to pump insertion into a larger cavity from measured inlet pressure. Non-adjusted stage efficiency takes into account only the adjusted motor power.

As shown in FIGS. 11C-11F, the reversed curved vane inlet stator had higher current and torque ratings for corresponding conditions and also proved to have better efficiency while pumping at 3 LPM.

From the data of FIGS. 11A-11F, it will be appreciated that the reversed curve inlet vane configuration improves the overall performance of the pump in comparison with a conventional straight vane inlet vane configuration. Thus, at the same speed, a pump fitted with the reversed curve inlet vanes will have a higher output flow. Similarly, to achieve the same output, the pump fitted with the reversed curve inlet vanes will operate at a lower speed. Because, of this, blood shear and resulting thrombosis formation can be reduced. This may also help reduce pump power consumption and extend battery life.

Referring to FIG. 2E, to help further the performance of the pump 20, the pump may include an outlet stator 88 in addition to the inlet stator 46. The outlet stator 88 is constructed in a manner and with materials similar or identical to those described above in regard to the inlet stator 46. The outlet stator 88 turns the flow from the impeller 40 and helps decelerate the flow efficiently and direct the flow through the pump outlet 26. As shown in FIG. 2E, the blades 90 of the inlet stator 46 and outlet stator 88 have a variable thickness from leading edge to trailing edge. This generally tapered shape can be tailored to help lower drag and thereby reduce pressure drop.

Referring to FIGS. 2B and 2C, the impeller 40 may include a shroud 48 that helps to further improve the pump performance. The shroud 48 has a generally cylindrical configuration and may be formed as a single piece of material with the impeller 40 or may be formed separately and subsequently attached to the impeller. The shroud 48 adds damping which helps stabilize the dynamics of the impeller 40 and/or rotor assembly 120.

Referring to FIGS. 2B-2D, the impeller 40 includes a hub 82 and a plurality of impeller blades 80 that project outwardly from the hub. The blades 80 project from the hub 82 in a curved or curvilinear manner, as best shown in FIGS. 2C and 2D. Referring to FIG. 2D, the blades 80 each have a curved leading edge 84. The curve of the leading edge 84 is configured such that the blade angle varies from the hub 82 to the tip 86 of the blade. As illustrated at a and 13 in FIG. 2D, the blade angle at locations on the blades 80 increase as the location moves from the hub 82 toward the tip 86. This helps compensate for the fact that, as the diameter of the impeller 40 increases, the local blade speed increases. Varying the blade angle at the leading edge 86 helps to better match the flow angle with the blade angle.

Figure 4A:
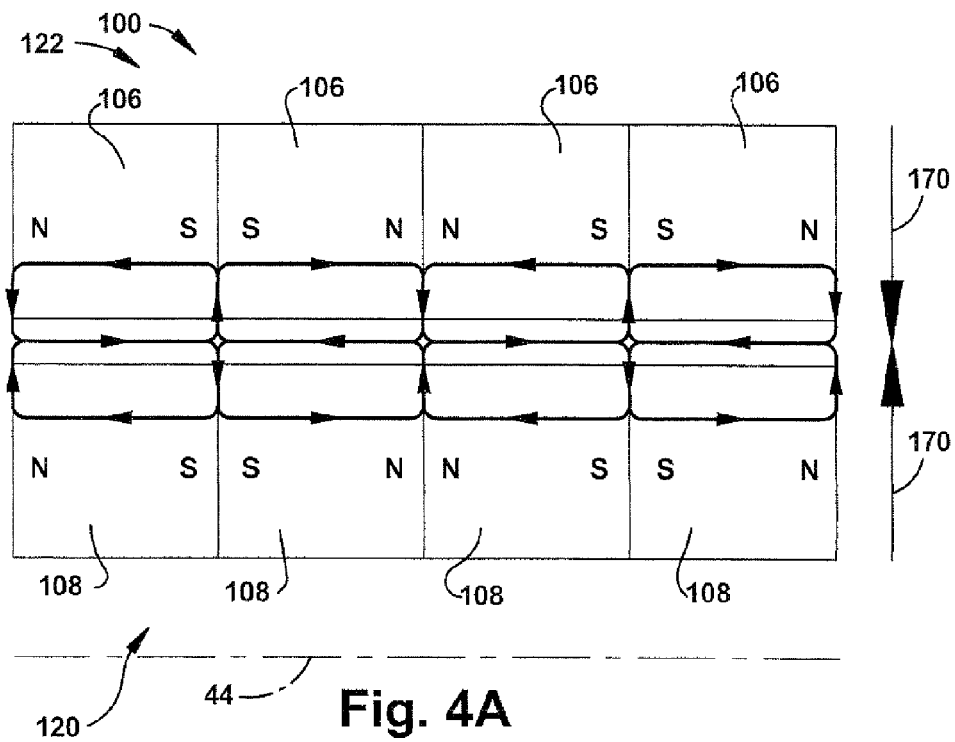
FIGS. 4A and 4B are schematic illustrations of a portion of the pump of FIG. 2A.
Figure 4B:
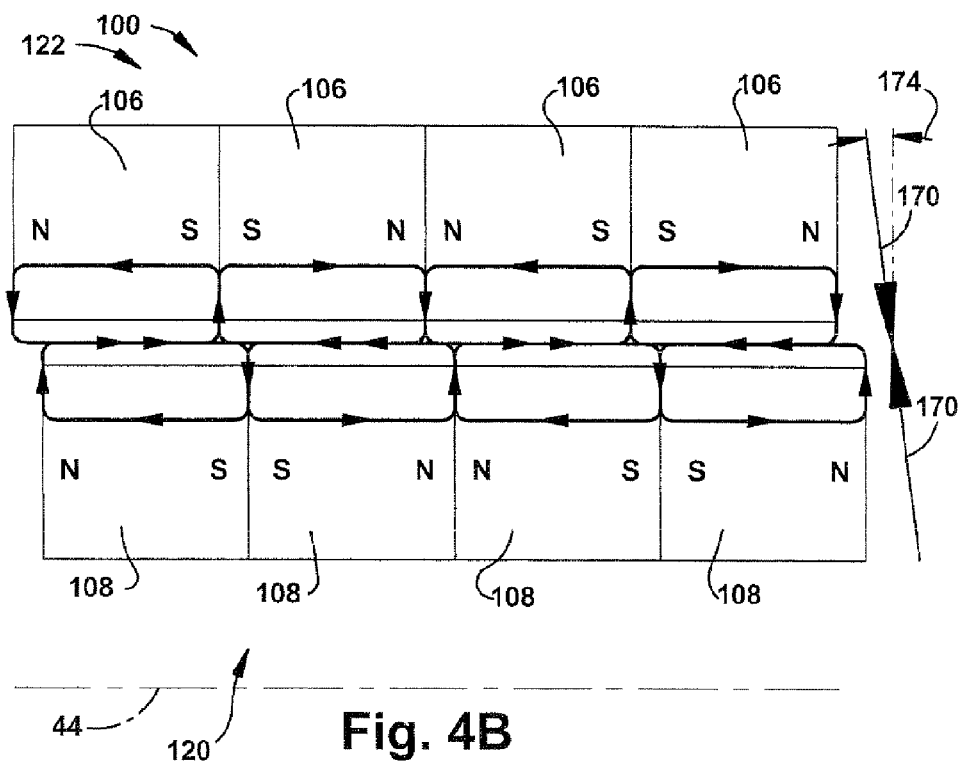

Referring to FIGS. 4A and 4B, the radial bearings 100 operate on a repulsive force principle. Each pair of permanent magnet (PM) rings 106 and 108 has north and south poles aligned in the radial direction. In operation, the radial bearings 100 help overcome the side pull of the motor 50 and maintain the rotor assembly 120 suspended relative to the stator assembly 122. The radial bearings 100 also have an axial stiffness that, in combination with hydraulic forces, helps determine the position of the rotor assembly 120 relative to the stator assembly 122. To increase the bearing stiffness, the neighboring PM stator rings 106 and rotor rings 108 are placed in opposing polarity, i.e., north-to-north and south-to-south. The non-ferromagnetic construction of the pump components adjacent the radial bearings 100 helps maintain the magnetic flux paths of the magnets 106 and 108, which helps achieve a relatively low axial side pull during operation of the pump 20. The PM stator magnets 106 may extend 360° about the rotor assembly 120. Alternatively, one or more of the PM stator magnets 106 may extend less than 360° about the rotor assembly 120. This may help produce a net magnetic force that helps stabilize the submerged rotor assembly 120 during use.

FIGS. 4A and 4B illustrate an unstable equilibrium condition and an axially offset condition, respectively, of the radial bearings 100. Referring to FIG. 4A, in the unstable equilibrium condition of the radial bearings 100, the magnetic poles of the rotor magnets 108 and stator magnets 106 are axially aligned with each other. This is the desired condition of the radial bearings 100 during operation of the pump 20 because, when the bearings are in this position, the rotor assembly 120 is in a position in which the axial bearings 140 are not loaded. The magnetic flux paths resulting from this arrangement are indicated generally by the arrows in the rotor magnets 108 and stator magnets 106. In this axially aligned position, the flux paths are aligned and the attractive/repulsive forces of the magnets 106 and 108 acting on the stator assembly 122 and rotor assembly 120 are radial in nature, as shown by the arrows identified at 170 in FIG. 4A.

Referring to FIG. 4B, in the axially offset condition of the radial bearings 100, the magnetic poles of the rotor magnets 108 and stator magnets 106 are offset from each other along the axis of rotation 44. This distance may be relatively small (e.g., 0.0002-0.002 in.). This is the pre-loaded, axially offset condition prior to operation of the pump 20. The magnetic flux paths resulting from this arrangement are indicated generally by the arrows in the rotor magnets 108 and stator magnets 106. In this axially offset position, the flux paths are misaligned and the attractive/repulsive forces of the magnets 106 and 108 acting on the stator assembly 122 and rotor assembly 120 have radial components, as shown by the arrows identified at 172 in FIG. 4B, and axial components, as shown by the arrows identified at 174 in FIG. 4B.

According to the present invention, the pump 20 is constructed to produce a net axial force that urges the rotor assembly 120 to move axially relative to the stator assembly 122 to the axially offset condition of FIG. 4B. To achieve this, the rear stop 156 of the rear axial bearing 144 and the front stop 152 of the front axial bearing 142 are moved rearward from the positions that would maintain the radial bearings 100 at the unstable equilibrium point. As a result, when the pump 20 is at rest, the rotor assembly 120 moves rearward against the rear stop 156 under the net axial pull of the radial bearing magnets 106 and 108 to the axially offset condition of FIG. 4B.

According to the present invention, the thrust of energy transfer to the fluid by the impeller 40 and the static pressure gradient front to back on the rotor assembly 120 produce hydrodynamic forces that counteract the net axial force of the radial bearing misalignment and help move the magnets 106 and 108 toward the unstable equilibrium condition of FIG. 4A. In operation of the pump 20, fluctuations in applied load, such as those resulting from the natural heart beat of the patient, result in a cyclical front-to-back oscillation of the rotor assembly 120 relative to the stator assembly 122. This helps cycle the loads on the axial bearings 140, which helps reduce friction and heat in the bearings and also helps produce a cyclical washing of the bearings. As a result, these cyclical loads help prevent thrombosis formation in the pump 20 by permitting cyclical washing at the front and rear stops 152 and 156.

According to the present invention, the front stop 152, the rear stop 156, or both, may be configured with features that help create axial forces that help minimize or eliminate contact forces when the rotor assembly 120 comes close to the contact point. Two such features are illustrated in FIGS. 2F-2H. FIGS. 2F-2H illustrate by way of example the rear stop point 156. It will be appreciated, however, that the features of FIGS. 2F-2H could be implemented in the rear stop point 156, the front stop point 152, or both.

Referring to FIGS. 2F-2H, the stop point 156 includes a permanent magnet axial bearing 160 that exerts an axial force on the rotor assembly 120. The force exerted on the rotor assembly 120 by the bearing 160 opposes axial forces placed on the rotor assembly by the radial bearings 100 and helps eliminate occasional mechanical contact at the stop point 156. The stop point 156 also includes surface profiles, such as recesses 162. As shown in FIGS. 2G and 2H, the surface profiles 162 have a generally concave curved configuration and are recessed into the surface of the stop point 156. The profiles 162 help generate hydrodynamic lifting forces that help minimize or eliminate contact forces when the rotor 120 comes very close to the stop point 156. These hydrodynamic forces help counteract the residuals from the summing of the other axial forces acting on the rotor 120.

The pump 20 may be configured for a number of different implementations, including intravascular and intracorporeal extravascular implementations, as appropriate for patient size. Intravascular implementations may be used for larger patients, such as larger pediatric patients through adolescence and adulthood. Intracorporeal extravascular implementations may be used for smaller patients, such as neonatal and very young pediatric patients. The pump 20 illustrated in the embodiment of FIGS. 1-3 is configured for intravascular implementations. Examples of these intravascular implementations are shown in FIGS. 5A-5C.

Figure 5A:
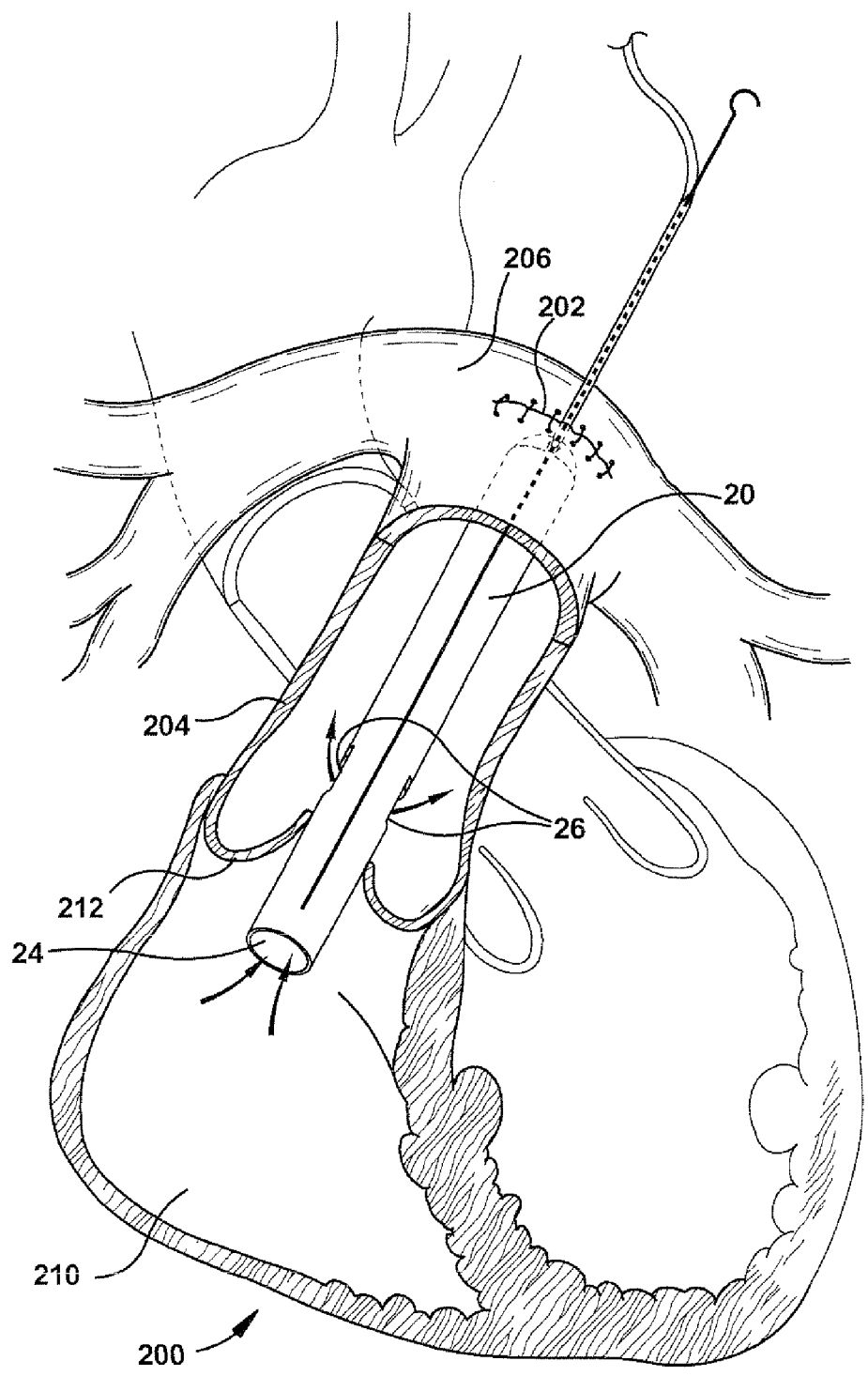
FIGS. 5A and 5B illustrate different implementations of the pump of FIG. 2A.

Referring to FIG. 5A, the pump 20 is shown in an intravascular implementation as a right ventricular assist device (RVAD). In the RVAD implementation, the pump 20 is inserted into the heart 200 through an incision 202 in the pulmonary artery 206 at the intersection of the pulmonary trunk 204 and the pulmonary artery. The pump 20 is positioned with the inlet 24 extending through the pulmonary semilunar valve 212 into the right ventricle 210 and the outlet 26 positioned in the pulmonary trunk 204. In operation, the pump 20 operates as described above to assist the right ventricle 210 in pumping blood to the pulmonary artery 206.

Figure 5B:
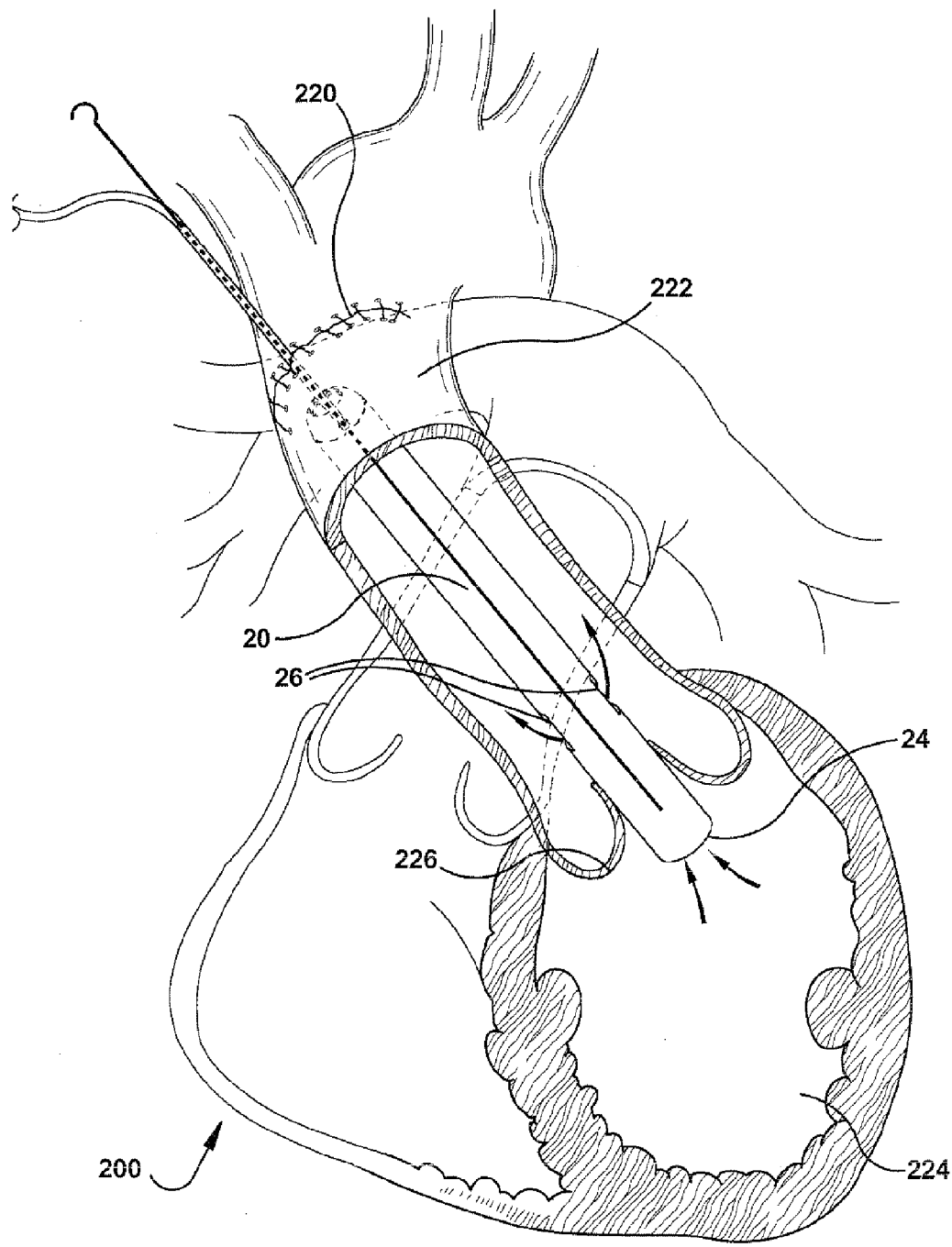

Referring to FIG. 5B, the pump 20 is shown in an intravascular implementation as a left ventricular assist device (LVAD). In the LVAD implementation, the pump 20 is inserted into the heart 200 through an incision 220 in the aorta 222. The pump 20 is positioned with the inlet 24 extending through the aortic semilunar valve 226 into the left ventricle 224 and the outlet 26 positioned in the aorta 222. In operation, the pump 20 operates as described above to assist the left ventricle 224 in pumping blood to the aorta 222.

Figure 5C:
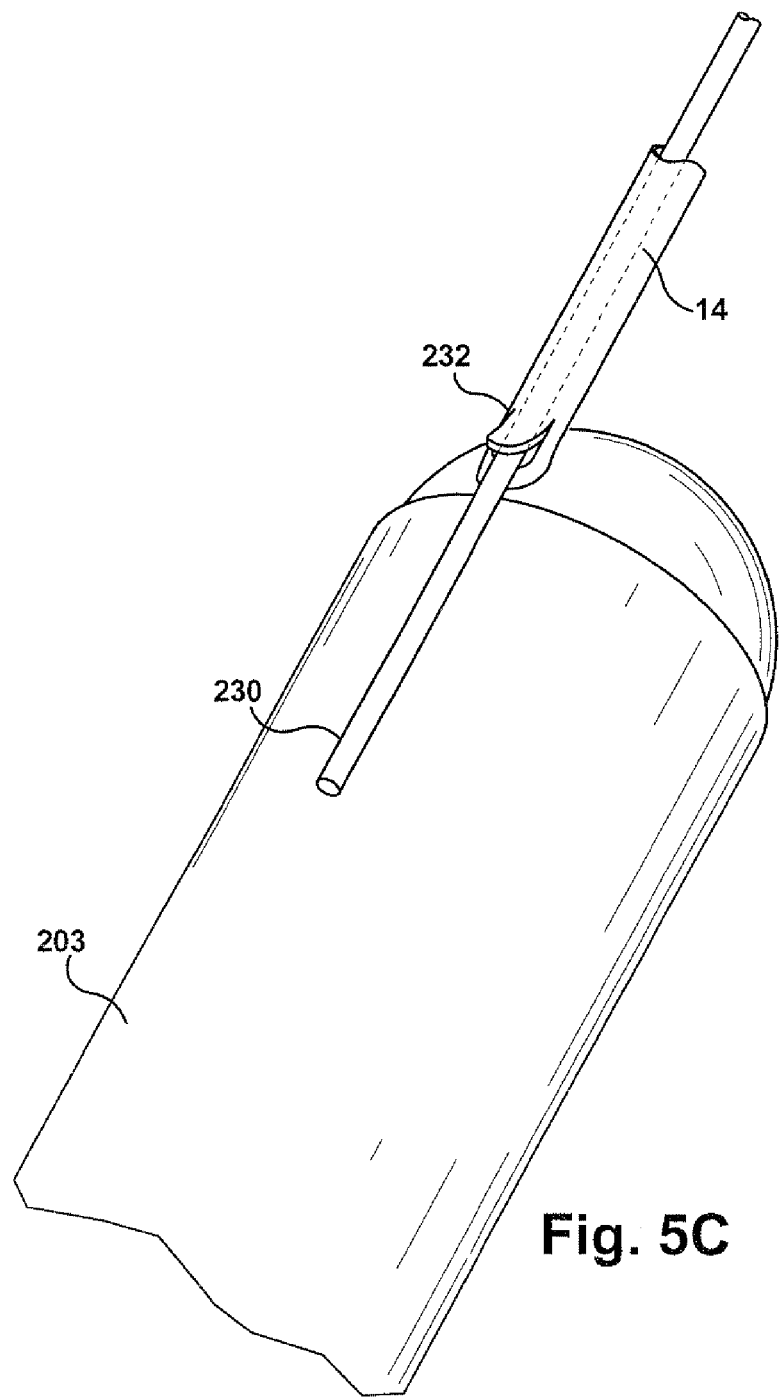
FIG. 5C illustrates a guide wire feature of the pump of FIG. 2A.

Referring to FIGS. 5A-5C, the pump 20 is fitted with a guide wire 230 that helps direct the pump into the desired position in the heart 200. The guide wire 230 extends through a sheath or cover 232 of the power cable 14 of the pump 20, exiting through an opening 234 adjacent or near the location where the cable enters the pump. The sheath 232 includes a flap 236 that covers and closes the opening 234 when the guide wire 230 is removed. The guide wire may be constructed of a suitable material, such as stainless steel or titanium, selected to exhibit a desired combination of physical properties, such as strength and ductility, that allow the guide wire to be deformable to a desired shape and capable of maintaining the desired shape.

Referring to FIGS. 5A and 5B, the guide wire 230 and pump 20 are inserted into the heart 200 through the incisions 202 and 220. The guide wire 230 may be advanced forward of the pump 20 and guided to the desired location in the organ, i.e., the right ventricle 210 or left ventricle 224. The pump 20 can then be delivered to the desired location using the stiffened guide wire 230 to maneuver and guide placement of the pump. The position of the pump 20 can then be adjusted by sliding the sheath 232 of the power cable 14 over the guide wire 230.

Figure 5D:
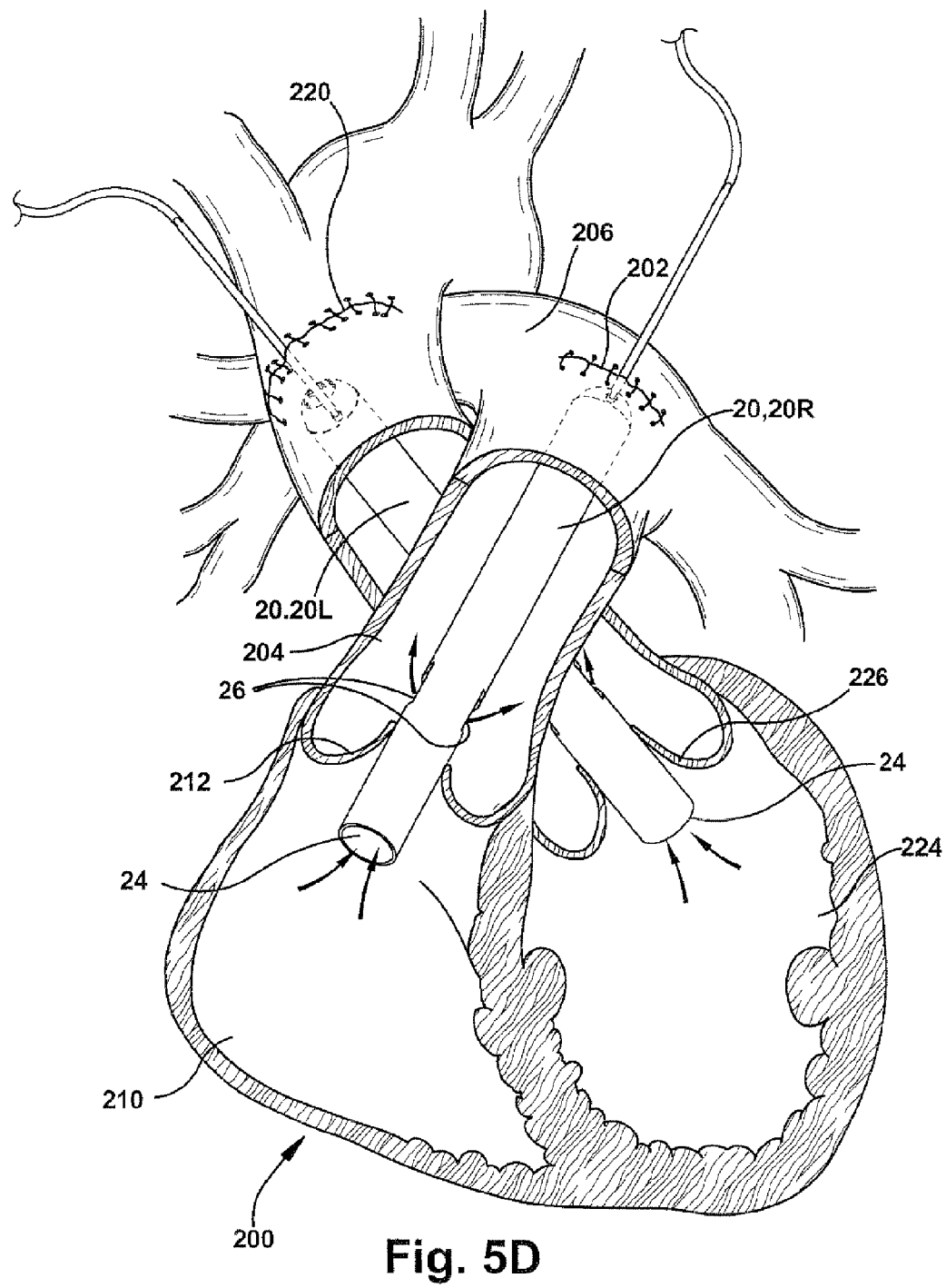
FIG. 5D illustrates another implementation of the pump of FIG. 2A.

Referring to FIG. 5D, two pumps 20 are shown in an intravascular implementation as bi-ventricular assist devices (BVAD). Essentially, the BVAD implementation incorporates two pumps 20 arranged in the RVAD and an LVAD implementations described above in FIGS. 5A and 5B. In FIG. 5D, the guide wire 230 of FIGS. 5A-5C is not shown for purposes of illustrating the pumps 20 with out this feature. The guide wire 230 of FIGS. 5A-5C is suited for use in the BVAD implementation of FIG. 5D. Thus, in the BVAD implementation, an RVAD pump 20R is inserted through an incision 202 in the pulmonary artery 206 and is oriented with the inlet 24 positioned in the right ventricle 210 and the outlet 26 positioned in the pulmonary trunk 204. An LVAD pump 20L is inserted through an incision 220 in the aorta 222 and is oriented with the inlet 24 positioned in the left ventricle 224 and the outlet 26 positioned in the aorta 222. In operation, the RVAD pump 20R assists the right ventricle 210 in pumping blood to the pulmonary artery 206 and the LVAD pump 20L assists the left ventricle 224 in pumping blood to the aorta 222.

Figure 6:
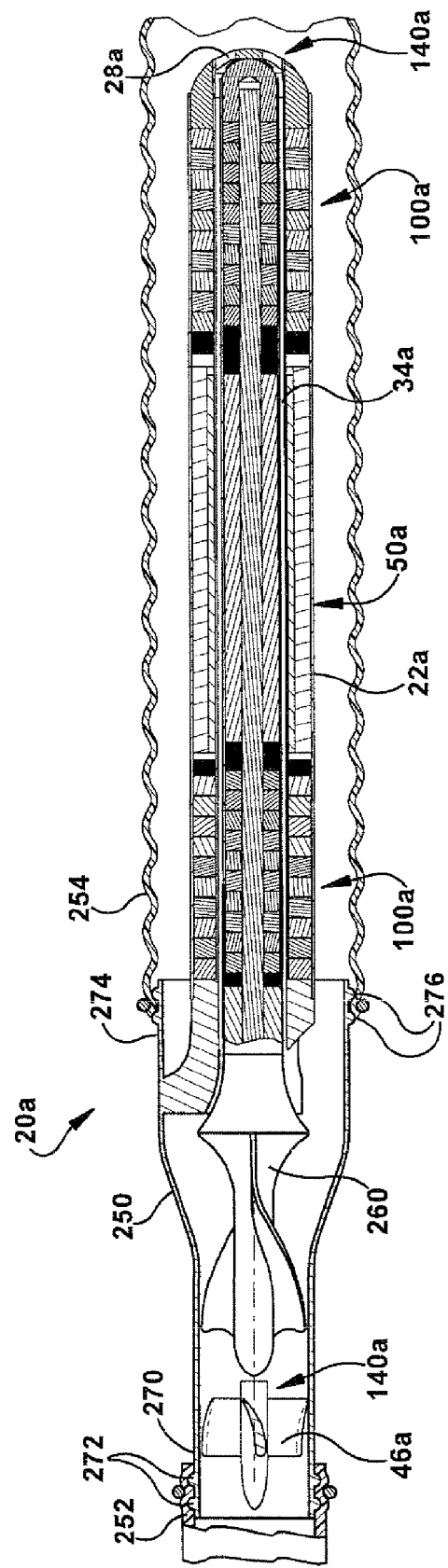
FIG. 6 is a sectional view of a blood pump of the blood pumping system of FIG. 1, according to a second embodiment of the present invention.

A second embodiment of the present invention is illustrated in FIG. 6. The second embodiment of the invention is similar to the first embodiment of the invention illustrated in FIGS. 1-5D. Accordingly, numerals similar to those of FIGS. 1-5D will be utilized in FIG. 6 to identify similar components, the suffix letter "a" being associated with the numerals of FIG. 6 to avoid confusion. According to the second embodiment, the pump 20a is configured for intracorporeal extravascular RVAD, LVAD, or BVAD implementations. To accomplish this, the pump 20a of the second embodiment includes an attached catheter or cannula that facilitates insertion in the heart and a catherter or graft to facilitate connection to the vasculature. The catheter or cannula is axially deformable, radially non-collapsible, and impermeable under the physiological and biological conditions associated with the blood pump usages described herein.

Referring to FIG. 6, the pump 20a includes a pump head housing 250 configured to accommodate an inlet catheter or cannula 252 and an outlet catheter or cannula 252. As shown in FIG. 6, the pump 20a also includes an impeller 260, accommodated in the pump housing 250, that has a configuration varied from that of the first embodiment. Components other than the pump head housing 250 and the impeller 260 (e.g., the inlet stator 46a, motor 50a, radial bearings 100a and axial bearings 140a) may be similar or identical to that shown and described in conjunction with the first embodiment of FIGS. 1-5D.

The pump head housing 250 includes an inlet portion 270 connectable with the inlet cannula 252 and an outlet portion 274 connectable with the outlet cannula 254. The inlet portion 270 may include means 272, such as ribs on an outer surface of the inlet portion, that facilitate a secure and reliable connection between the inlet portion and the inlet cannula 252. Likewise, the outlet portion 274 may include means 276, such as ribs on an outer surface of the outlet portion, that facilitate a secure and reliable connection between the outlet portion and the outlet cannula 254. This connection may be facilitated, for example, by a wire loop retainer or a threaded clamp retainer.

The configuration of the pump head housing 250 of the second embodiment helps facilitate extravascular implementations of the pump 20a. More particularly, the pump head housing 250 helps facilitate discharging blood along the outside diameter of the motor/bearing housing 22a into the outlet cannula 254. The configuration of FIG. 6 permits wash flow in the motor gap 34a through the wash flow ports 28a under the influence of arterial pressure. As an additional feature of the embodiment of FIG. 6, the primary flow, being contained within the outlet cannula 254 next to the motor 50a and motor housing 22a, may also have some enhanced cooling effects on the motor. Since the primary flow of the pump 20a is outside the pump rather than through the motor gap 34a, the motor gap can be kept at a minimum size, which helps reduce the overall diameter and size of the pump.

Figure 7A:
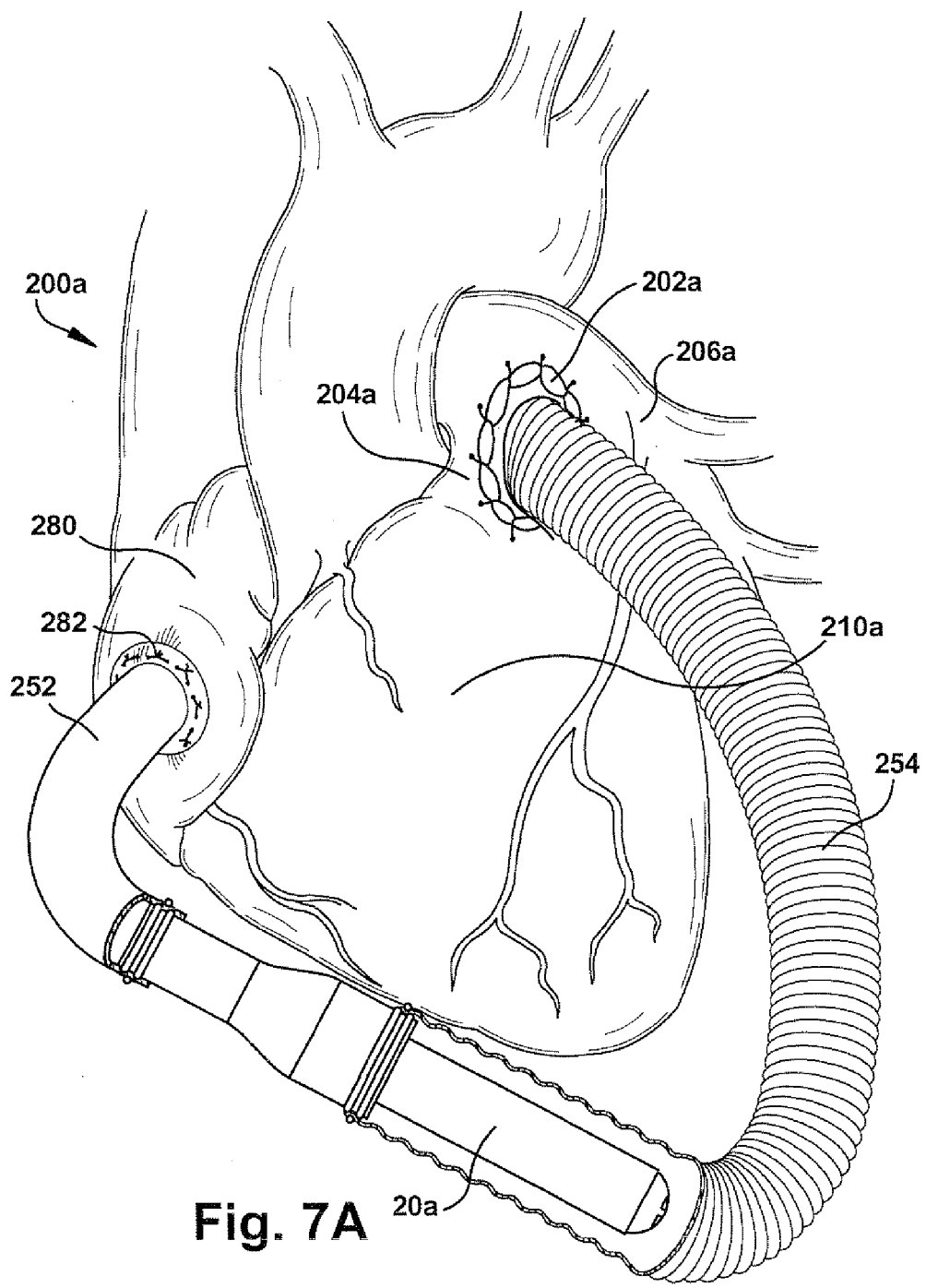
FIGS. 7A-7C illustrate different implementations of the pump of FIG. 6.
Figure 7B:
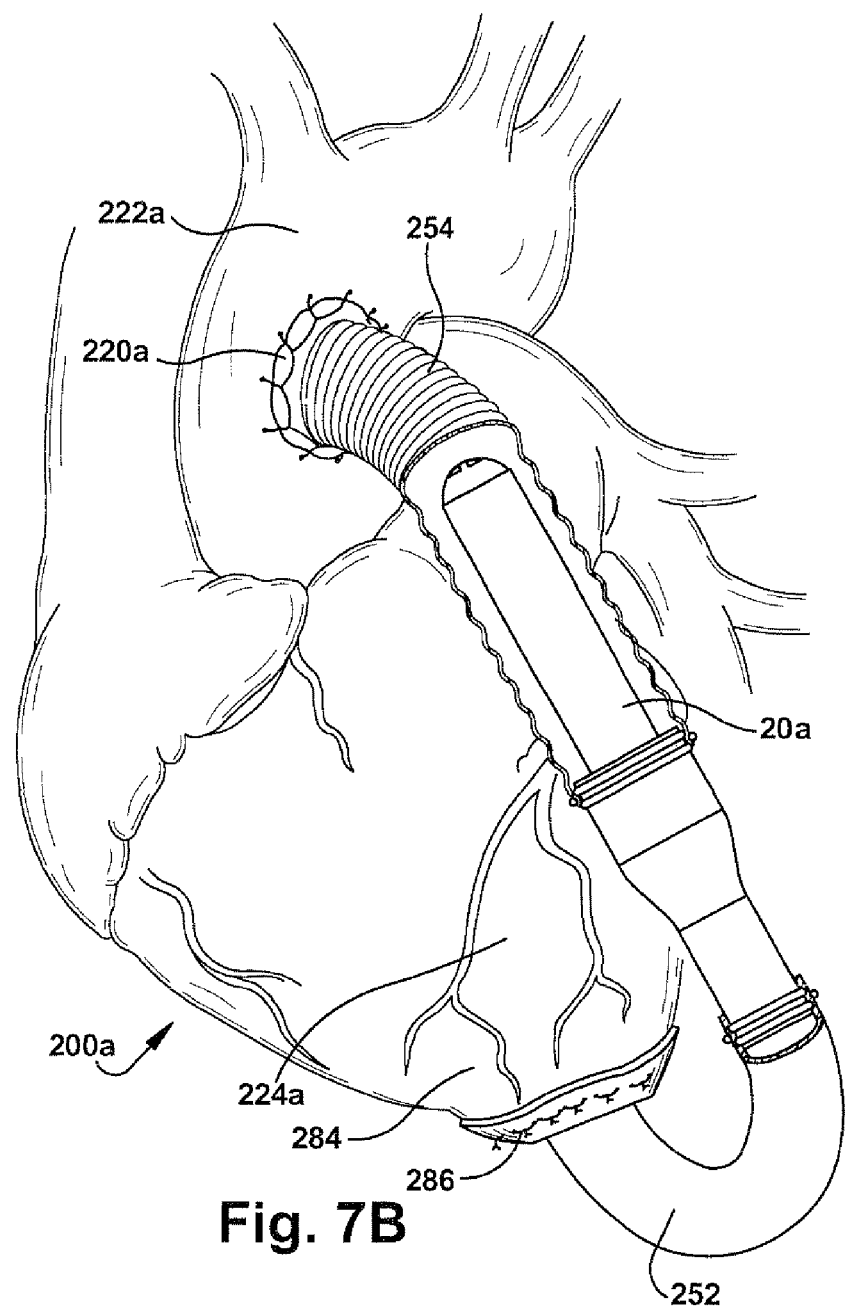
Figure 7C:
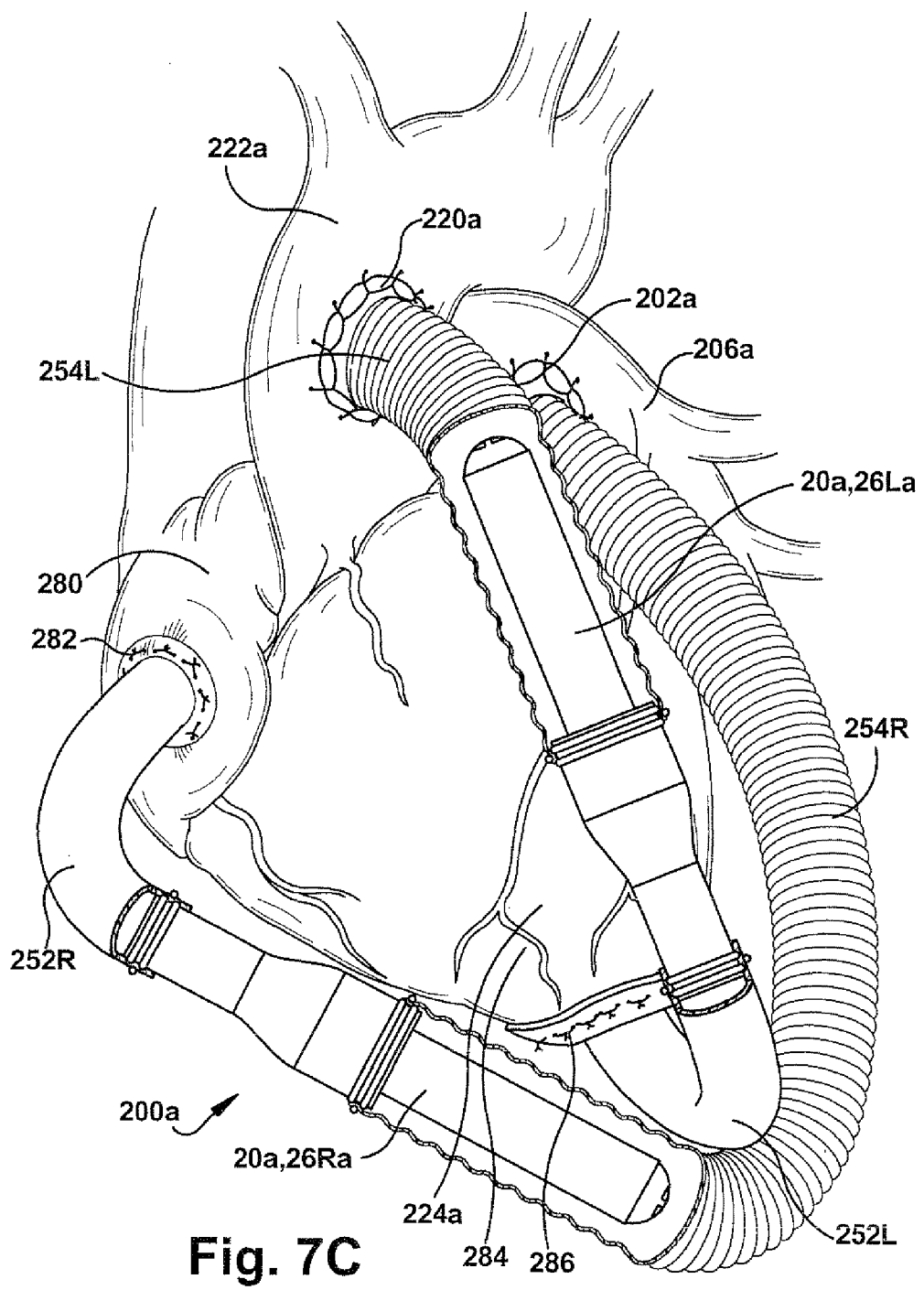

FIGS. 7A-7C illustrate intracorporeal extravascular implementations of the pump 20a of FIG. 6. Referring to FIG. 7A, the pump 20a is shown in an intracorporeal extravascular RVAD implementation. In this RVAD implementation, the pump 20a is implanted in the patient next to the heart 200a. The outlet cannula 254 is connected via incision 202a to the pulmonary artery 206a at the intersection of the pulmonary trunk 204a and the pulmonary artery. The inlet cannula 252 is connected via incision 282 to the right atrium 280 or, alternatively, the right ventricle 210a. In operation, the pump 20a operates as described above to assist the right ventricle 210a by pumping blood from the right atrium 280 through the inlet cannula 252 to the pulmonary artery 206a via the outlet cannula 254.

Referring to FIG. 7B, the pump 20a is shown in an intracorporeal extravascular LVAD implementation. In this LVAD implementation, the pump 20a is implanted in the patient next to the heart 200a. The outlet cannula 254 is connected via incision 220a to the aorta 222a. The inlet cannula 252 is connected via incision 286 to the apex 284 of the left ventricle 224a or, alternatively, the left atrium. In operation, the pump 20a operates as described above to assist the left ventricle 224a by pumping blood from the left ventricle through the inlet cannula 252 to the aorta 222a via the outlet cannula 254.

Referring to FIG. 7C, two pumps 20a are shown in an intracorporeal extravascular implementation as bi-ventricular assist devices (BVAD). Essentially, the BVAD implementation incorporates two pumps 20a arranged in the RVAD and an LVAD implementations described above in FIGS. 7A and 7B. An RVAD pump 20Ra is implanted in the patient next to the heart 200a. The outlet cannula 254R is connected via incision 202a to the pulmonary artery 206a and the inlet cannula 252R is connected via incision 282 to the right atrium 280 or, alternatively, the right ventricle. An LVAD pump 20La is implanted in the patient next to the heart 200a. The outlet cannula 254L is connected via incision 220a to the aorta 222a and the inlet cannula 252L is connected via incision 286 to the apex 284 of the left ventricle 224a or, alternatively, the left atrium. In operation, the RVAD pump 20Ra assists the right ventricle 210a by pumping blood from the right atrium 280 through the inlet cannula 252R to the pulmonary artery 206a via the outlet cannula 254R. In operation, the LVAD pump 20La assists the left ventricle 224a by pumping blood from the left ventricle through the inlet cannula 252L to the aorta 222a via the outlet cannula 254L.

Figure 8A:
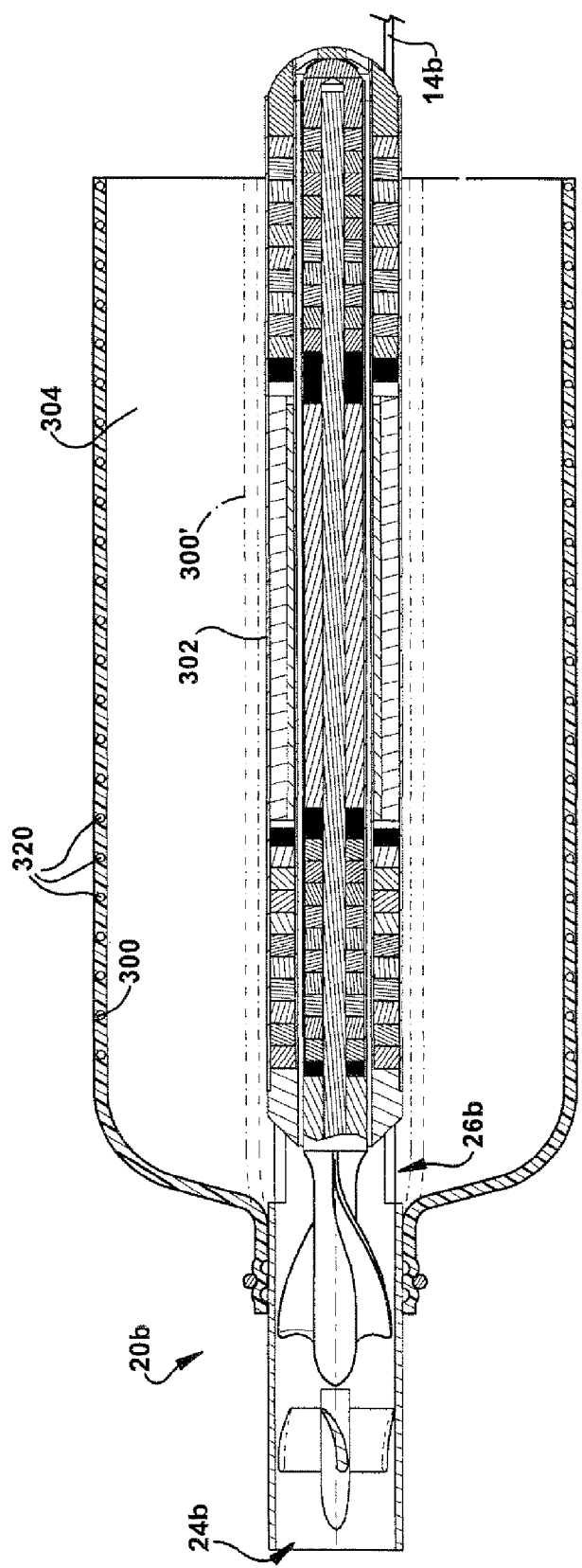
FIG. 8A is a sectional view of the pump of FIG. 2A outfitted with an outflow sheath in accordance with a third embodiment of the present invention.
Figure 8B:
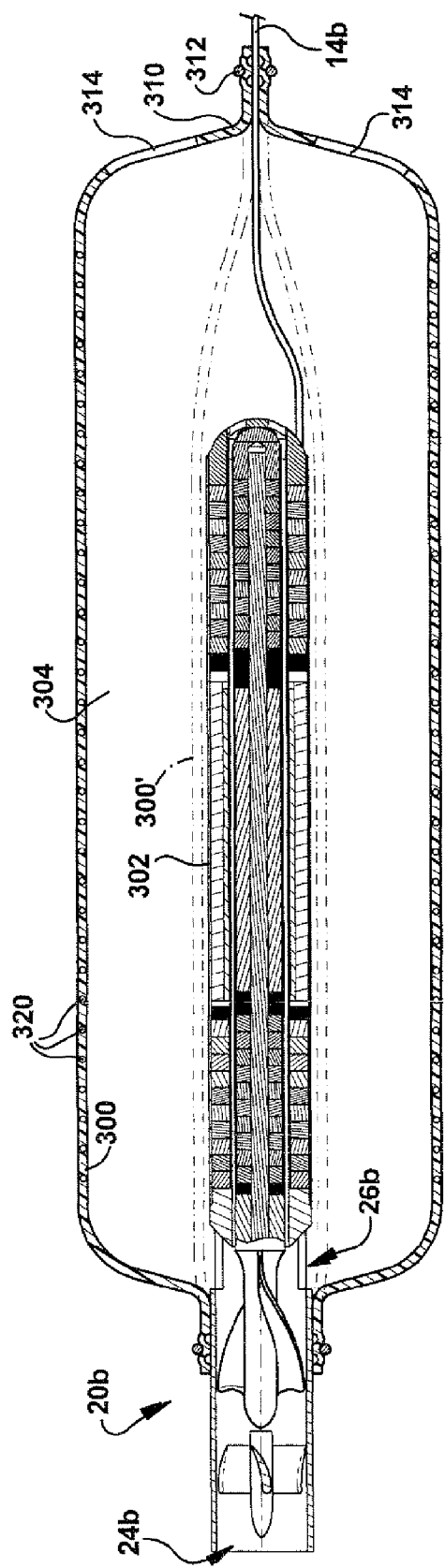
FIG. 8B is a sectional view illustrating an alternative construction of the pump of FIG. 8A.
Figure 9:
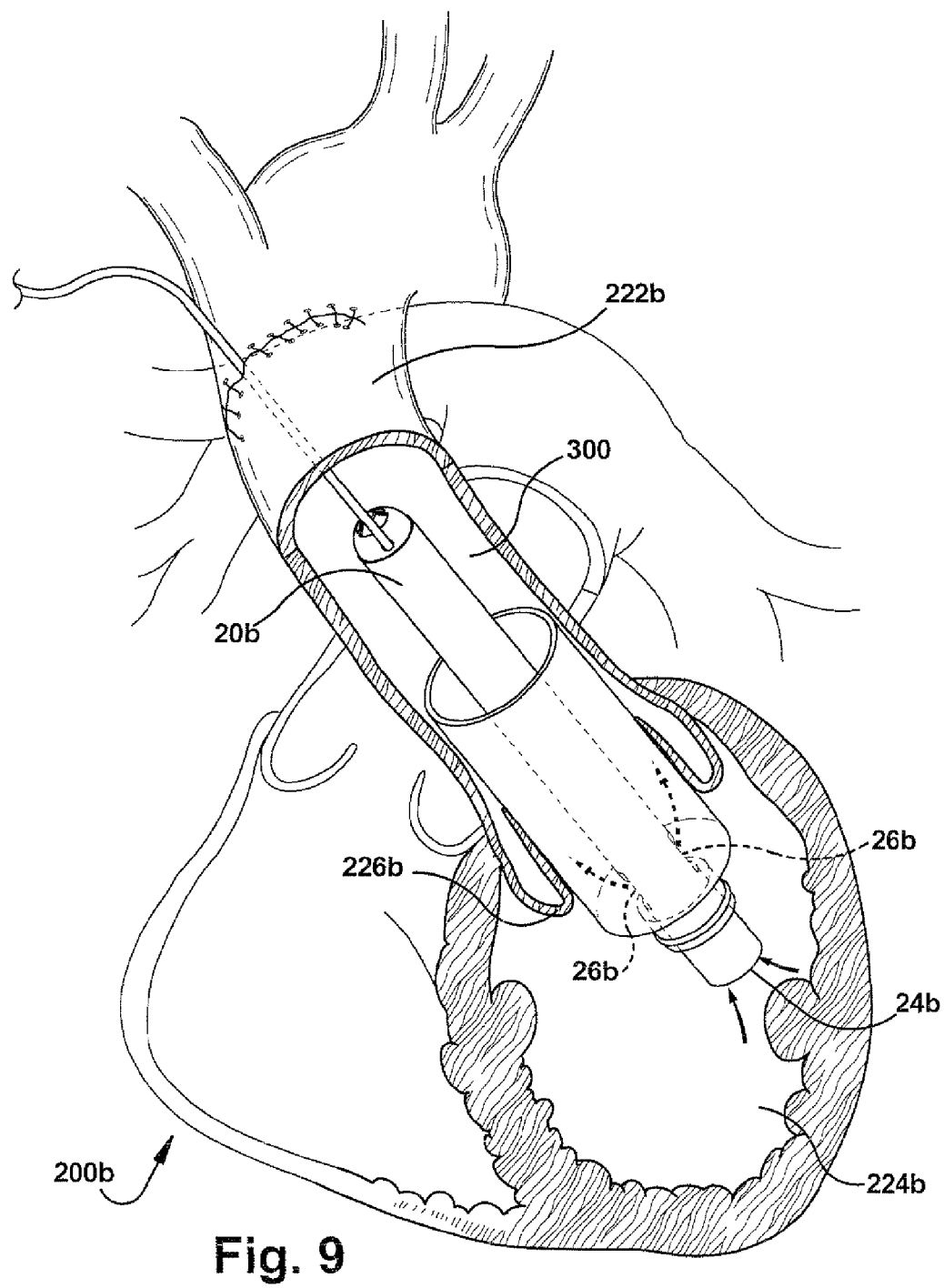
FIG. 9 illustrates the pump of FIG. 8A in an activated condition.

A third embodiment of the present invention is illustrated in FIGS. 8A-9. The third embodiment of the invention is similar to the first embodiment of the invention illustrated in FIGS. 1-5D. Accordingly, numerals similar to those of FIGS. 1-5D will be utilized in FIGS. 8A-9 to identify similar components, the suffix letter "b" being associated with the numerals of FIGS. 8A-9 to avoid confusion.

According to the third embodiment, the pump 20b is fit with an outflow sheath 300 for directing the primary mixed flow along the outside of the pump. The outflow sheath 300 has a flexible construction that allows the sheath to be wrapped around an outer surface 302 of the pump 20b during implantation. This is shown in dashed lines at 300' in FIGS. 8A and 8B. During operation of the pump 20b, the flow expands and unwraps the sheath 300 to the position shown in solid lines at 300 in FIGS. 8A-9. This allows the flow to pass through a radial space 304 defined between the pump 20b and the sheath 300. As shown in FIGS. 8A and 8B, the sheath 300 may include means 320, such as wire bands or a helical coil, that helps limit expansion of the sheath to a desired diameter. The means 320 could, for example, be molded or extruded with the sheath 300 or bonded to the sheath.

Referring to FIG. 8B, in an alternative configuration, the outflow sheath 300 has an end portion 310 connected with the power cable 14b of the pump 20b. This helps resist migration of the sheath 30 back along the outer surface 302 of the pump 20b. The end portion 310 is connected to the power cable 14b by means 312, such as a clamp. Because the sheath 300 is clamped to the power cable 14b, outlet flow openings 314 are formed in the sheath 300.

The sheath 300 allows for reducing the overall size of the pump 20b. For reference, referring back to the embodiment of FIGS. 5A-5D, those skilled in the art will appreciate that, for intravascular implementations of a pump that is not fit with a sheath 300, the pump extends through the heart valve and is positioned with the inlet and outlet positioned on opposite sides of the valve. For example, in an LVAD implementation, the pump extends through the heart valve with the inlet positioned in the left ventricle and the outlet positioned in the aorta. As another example, in an RVAD implementation, the pump extends through the heart valve with the inlet positioned in the right ventricle and the outlet positioned in the pulmonary trunk. As shown in FIGS. 5A-5D, to achieve these extents, the pump has a configuration in which the inlet is extended to reach into the heart chamber while the outlet is positioned on the opposite side of the heart valve. Those skilled in the art, however, will appreciate that this may result in an unwanted pressure drop on the inlet side of the pump.

Referring to FIG. 9, according to the present invention, the sheath 300 functions to extend the outlet of the pump 20b, which eliminates the need to extend the inlet. FIG. 9 illustrates an implementation of the pump 20b of FIG. 8A. Those skilled in the art, however, will appreciate that the pump of FIG. 8B may also be used in the implementation of FIG. 9. In the LVAD implementation shown in FIG. 9, the inlet 24b and outlet 26b of the pump 20b are positioned in the heart chamber, i.e., the left ventricle 224b. The sheath 300, however, extends through the heart valve 226b into the aorta 222b and thereby effectively places the outlet in the aorta. It will be appreciated that, using this technique, the need for an inlet extension, and any resulting pressure drop, can be eliminated.

The materials used to construct the various components of the pump 20 are selected to provide a high degree of biocompatibility, corrosion resistance, and manufacturability. For example, materials such as titanium and stainless steel may used to achieve these properties. For performance reasons, the materials of the motor 50 and radial bearings 100 include items of poor corrosion resistance (e.g., copper windings and NdFeB magnets). These materials are dehydrated, plated as appropriate, and hermetically sealed within titanium enclosures. Blood contacting surfaces may be coated with a low-friction, wear resistant material, such as Teflon® or a diamond-like carbon material, to help achieve high blood compatibility and for wear resistance at the axial touch points. Infection resisting coatings may also be used to cover the exterior of the pump in order to resist bacterial colonization and growth around the pump within a tissue pocket.

The pump 20 also incorporates features that help provide high thrombus resistance without anticoagulation. One such feature is that all surfaces are continuously washed with flowing blood. There are no dead end spaces or crevice-like geometries. The back and forth oscillation of the rotor helps ensure that the blood contacting surfaces inside the pump, including the front and rear stop points 152 an 156, are washed. Also, most surfaces are slightly heated, which helps inhibit platelet aggregation. Further, the Teflon® and diamond-like carbon coatings applied to various pump surfaces may also help prevent coagulation. Another coating that may be used to help prevent coagulation is a synthetic cell membrane material.

The pump 20 may also include provisions for monitoring motor winding temperatures. Increased winding temperatures may, for example, be indicative of insufficient wash flow, which may result in damage to the blood or tissue. The temperature may be measured using a thermocouple, which requires the addition of hardware and wiring. Alternatively, according to the present invention, winding temperatures may be monitored by measuring the resistance in the motor windings 62 between commutations of the motor phases. The measured resistance can be used to detect increasing temperatures in the motor windings 62. Since the windings are electrically connected to the ECU 12 via the cable 14, these measurements may be implemented through reconfiguring the controller without reconfiguring the pump 20.

The pump 20 further incorporates features that help resist infection. There are at least three areas in which the risk of infection is of heightened concern: pump infection by bacteremia, pocket infections around implanted hardware, and driveline infections around percutaneous lines. By design, the pump 20 has no infusion or monitoring lines that could provide a contamination pathway directly from the environment to the blood stream. The pump 20 is implanted, which minimizes the number and size of skin penetrations, as well as potential for trauma to these sites. A single, small diameter, very low stiffness wire exits the skin, which minimizes chronic trauma to the site and facilitates healing around the wire surface, which is textured to encourage tissue in-growth. The surface area of the implanted pump 20 body is extremely small, limiting the potential bacterial load that could be carried into a skin pocket. The pump housing may be Teflon® coated, which may help limit bacterial colonization.

The construction of the pumps 20, 20A and 20B disclosed herein have small package sizes in comparison with other implantable VADs. This allows for implementation of the pump 20 in the various intravascular and intercorporeal extravascular LVAD, RVAD, and BVAD scenarios described above. The small package size of the pump 20 is made possible by a variety of factors. One such factor is that the primary flow of the pump 20 being placed outside the pump. Another factor is that the pump 20, operating at high RPM (up to 60,000 RPM or more), is able to produce a relatively high output from a relatively small displacement volume. Example configurations illustrating small package size characteristics of the pumps 20 and 20A are set forth in Table 1:

TABLE 1

|  | Intravascular Pump (FIG. 2A) | Intracorporeal Extravascular Pump (FIGS. 6, 8A, 8B) |
|---|---|---|
| Diameter, mm | 7 | 11 |
| Length, mm | 60 | 60 |
| Displaced Volume, ml | 2.3 | 4 |
| Pump Priming Volume, ml | 0.55 | 2.2 |
| Blood Contacting Surface Area, cm² | 15.8 | 33.5 |
| Weight, grams | 8.6 | 10.6 |

Figure 10A:
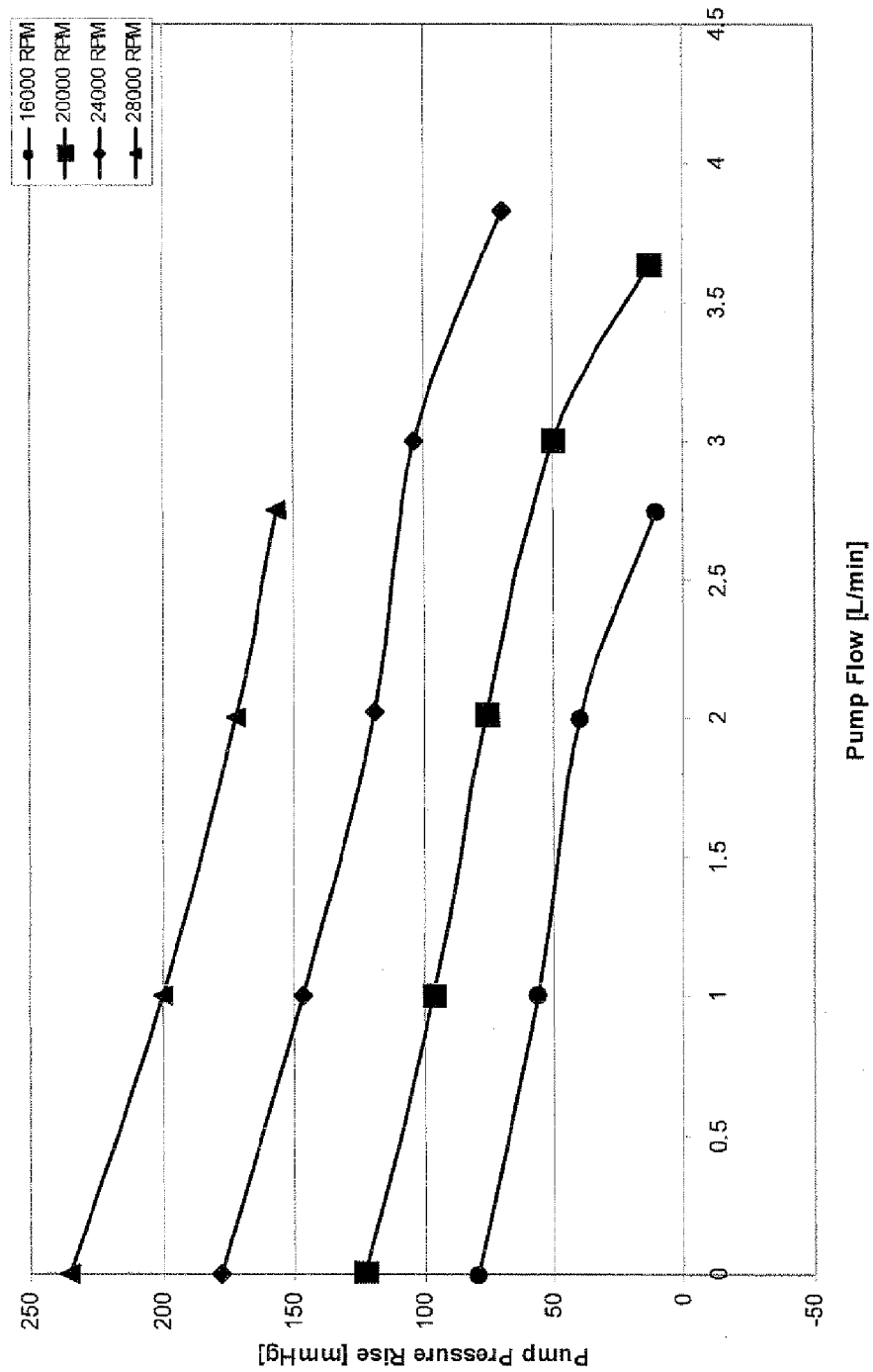
FIGS. 10A and 10B are charts illustrating pressure vs. flow characteristics for test configurations of the pumps of FIGS. 2A and 6, respectively.
Figure 10B:
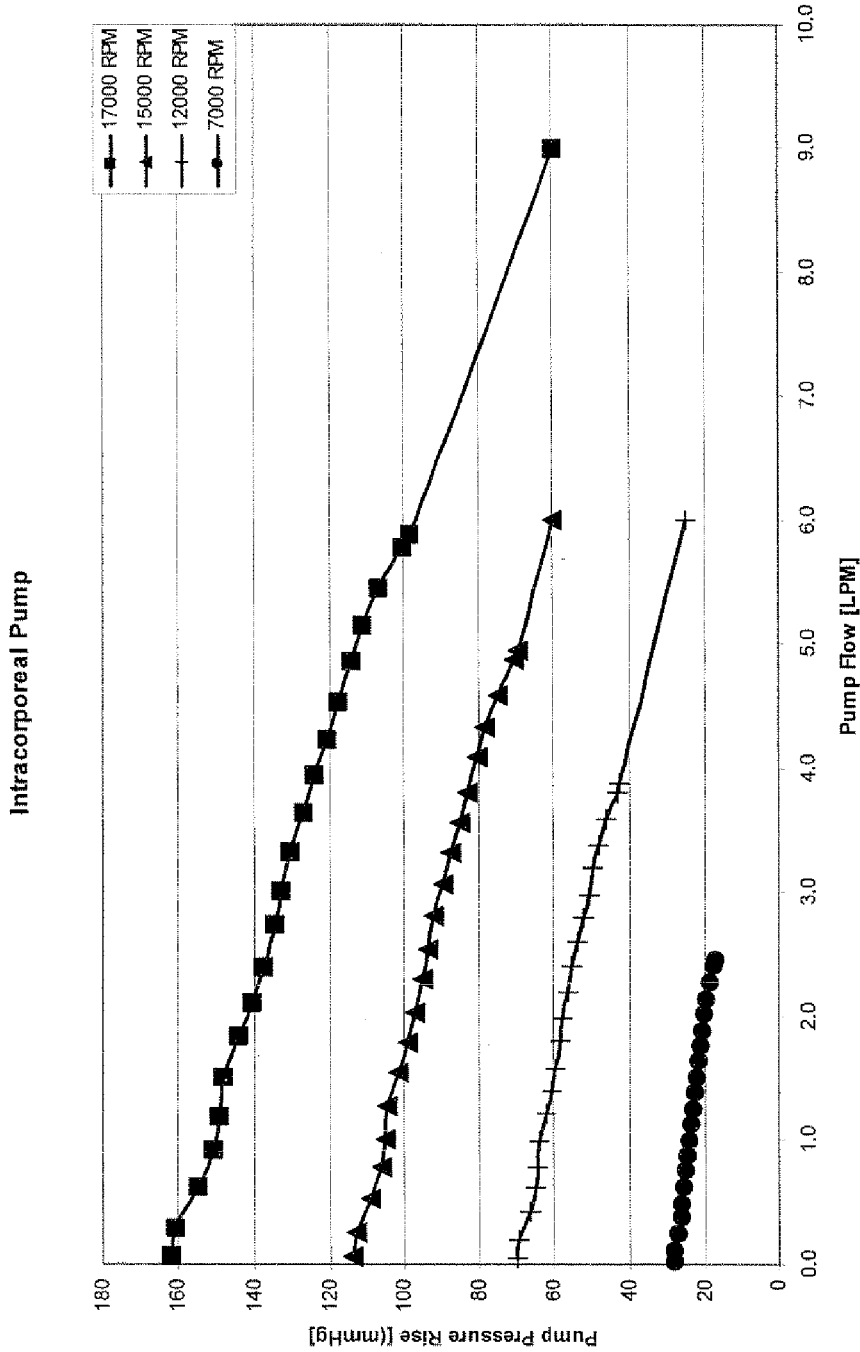

As shown in FIGS. 10A and 10B, even with the small package sizes shown in Table 1, the intravascular pump (see FIG. 2A) and the intracorporeal pump (see FIG. 6) are easily capable of operating at or around the nominal performance ratings for flow (3 LPM) and pressure (90 mmHg).

From the above description of the invention, those skilled in the art will perceive improvements, changes and modifications. Such improvements, changes and modifications within the skill of the art are intended to be covered by the appended claims.

Having described the invention, the following is claimed:

1. A blood pump comprising:
   a stator assembly comprising a motor stator, a fluid inlet, and a fluid outlet;
   a rotor assembly comprising a motor rotor and an impeller rotatable about an axis to move fluid from the inlet to the outlet; and
   a permanent magnet radial bearing for supporting the rotor assembly for rotation about the axis, the radial bearing being free from flux modulating coils and comprising:
   a permanent magnet radial bearing stator fixed to the stator assembly and a permanent magnet radial bearing rotor fixed to the rotor assembly, the radial bearing being configured such that the radial bearing stator magnets and the radial bearing rotor magnets are axially offset from each other when the pump is at rest.

2. The blood pump recited in claim 1, wherein the offset of the radial bearing stator magnets and the radial bearing rotor magnets is configured to balance with hydrodynamic forces created by pumping action of the impeller.

3. The blood pump recited in claim 1, further comprising front and rear stop points configured to limit an axial range of motion of the rotor assembly relative to the stator assembly in order to maintain the axial offset of the radial bearing stator magnets and the radial bearing rotor magnets.

4. The blood pump recited in claim 3, wherein at least one of the front and rear stop points comprises a magnetic axial bearing.

5. The blood pump recited in claim 3, wherein the stop points comprise surface profiles configured to generate hydrodynamic lifting forces.

6. The blood pump recited in claim 3, wherein the stop points are configured to prevent the radial bearing magnets from statically crossing over an unstable magnetic equilibrium point.

7. The blood pump recited in claim 3, wherein at least one of the front and rear axial stop points comprise a bearing surface that is formed with a synthetic jewel material, and a bearing surface that is formed with a ceramic material.

8. The blood pump recited in claim 3, wherein at least one of the front and rear stop points comprises a flat bearing surface on the stator and a curved bearing surface on the rotor.

9. The blood pump recited in claim 1, wherein the radial bearing stator comprises at least one permanent magnet that extends less than 360 degrees about the stator assembly.

10. The blood pump recited in claim 1, wherein:
    the radial bearing stator comprises a plurality of ring shaped stator magnets arranged next to each other in opposing polarity; and
    the radial bearing rotor comprises a plurality of ring shaped rotor magnets arranged next to each other in opposing polarity;
    the pump being configured such that, during operation, the stator magnets and rotor magnets are positioned with like polarities opposing each other.

11. The blood pump of claim 10, wherein the ring shaped rotor and stator magnets include a combination of axially and radially polarized elements.

12. The blood pump recited in claim 1, wherein the motor stator comprises an ironless motor stator.

13. The blood pump recited in claim 1, wherein the rotor has a 2-pole magnetic geometry.

14. The blood pump recited in claim 1, the motor stator further comprising a thin outer shell of magnetic material.

15. The blood pump recited in claim 1, wherein a radial motor gap is defined between the between the motor stator and the motor rotor, the pump being configured to direct a primary flow from the fluid inlet to the fluid outlet over an outside diameter of the motor stator and being configured to direct a wash flow through the motor gap.

16. The blood pump recited in claim 15, wherein the primary flow is discharged through the outlet at an intermediate angle having both axial and radial components so that the primary flow is directed along an outside surface of the stator assembly that extends the length of the motor stator.

17. The blood pump recited in claim 15, wherein the motor gap is defined at least partially by a surface having a non-circular cross-section.

18. The blood pump recited in claim 1, further comprising an inflow stator having vanes with a curvature reversed from the curvature of vanes on the impeller.

19. The blood pump recited in claim 1, further comprising an outflow sheath for helping to direct the primary flow along the outside of the pump.

20. The blood pump recited in claim 19, wherein the outflow sheath has a flexible construction that allows the sheath to be collapsed and wrapped around an outer surface of the pump for implantation.

21. The blood pump recited in claim 19, wherein the flow produced during operation of the pump expands the sheath to allow the flow to pass through a radial space defined between the pump and the sheath.

22. The blood pump recited in claim 19, further comprising a power cable for supplying electrical power to the blood pump, the power cable comprising an anchoring point for the sheath.

23. The blood pump recited in claim 19, further comprising reinforcing bands that help limit expansion of the sheath.

24. The blood pump recited in claim 19, wherein the sheath is effective to extend the fluid outlet axially downstream of the fluid inlet.

25. The blood pump recited in claim 19, wherein the sheath is secured to the stator assembly at a location positioned between the fluid inlet and the fluid outlet.

26. The blood pump recited in claim 19, wherein the sheath is constructed such that the fluid inlet and fluid outlet can be placed in a first location with the sheath extending along the outside of the pump and through a lumen into a second location, the sheath forming a conduit for directing pumped blood from the fluid outlet positioned in the first location through the lumen and into the second location.

27. The blood pump recited in claim 19, wherein the sheath is constructed such that the fluid inlet and fluid outlet can be placed in a left ventricle of the heart with the sheath extending along the outside of the pump and through a heart valve into the aorta, the sheath forming a conduit for directing pumped blood from the fluid outlet positioned in the left ventricle through the heart valve and into the aorta.

28. The blood pump recited in claim 19, wherein the sheath is constructed such that the fluid inlet and fluid outlet can be placed in a right ventricle of the heart with the sheath extending along the outside of the pump and through a heart valve into the pulmonary trunk, the sheath forming a conduit for directing pumped blood from the fluid outlet positioned in the right ventricle through the heart valve and into the pulmonary trunk.

29. The blood pump recited in claim 1, further comprising means for measuring a pump internal temperature as a pump control input.

30. The blood pump recited in claim 29, wherein the means for measuring the pump internal temperature comprises a motor winding resistance measurement.

31. The blood pump recited in claim 1, further comprising an attached catheter to facilitate insertion in a patient's heart from a remote location in the patient's circulatory tree.

32. The blood pump recited in claim 1, wherein the motor stator comprises motor windings that are formed in a racetrack shape.

33. The blood pump recited in claim 1, wherein the impeller comprises an impeller blade having a leading edge with an angle that varies from a hub of the impeller to a tip of the impeller blade.

34. The blood pump recited in claim 1, wherein the stator assembly further comprises at least one of an impeller inlet stator blade and an impeller outlet stator blade.

35. The blood pump recited in claim 34, wherein at least one of the impeller inlet stator blade and the impeller outlet stator blade has a variable thickness from a leading edge to a trailing edge.

36. The blood pump recited in claim 1, further comprising an inflow cannula that is axially deformable, radially non-collapsible, and impermeable.

37. The blood pump recited in claim 1, further comprising a biocompatible power cable configured to help support and advance the blood pump along a blood vessel.

38. The blood pump recited in claim 37, further comprising at least one channel in the power cable for receiving a guide wire.

39. The blood pump recited in claim 38, further comprising at least one guide wire insertable in the at least one channel.

40. The blood pump recited in claim 39, wherein the guide wire is deformable and configured so as to be capable of holding a deformed shape.

41. The blood pump recited in claim 38, wherein the channel is configured to facilitate advancing the guide wire ahead of the pump during placement.

42. The blood pump recited in claim 38, wherein the channel is configured to be self sealing when the wire is retracted into the cable.

43. The blood pump recited in claim 1, wherein the permanent magnet radial bearing stator consists essentially of one or more permanent magnets and the permanent magnet radial bearing rotor consists essentially of one or more permanent magnets.

44. A blood pump comprising:
 a housing comprising an elongated tubular side wall that extends along a central axis of the blood pump, the housing having a fluid inlet and a fluid outlet, the fluid outlet comprising at least one opening in the side wall;
 an impeller positioned in the housing for rotation about the axis, at least a portion of the impeller being positioned between the fluid inlet and the fluid outlet;
 a motor for imparting rotation of the impeller about the axis, the motor comprising:
 a stator fixed to the housing;
 a rotor coupled to the impeller; and
 a permanent magnet radial bearing for supporting the rotor for rotation about the axis, the radial bearing being free from flux modulating coils and comprising a permanent magnet radial bearing stator and a permanent magnet radial bearing rotor, the radial bearing being configured such that the radial bearing stator magnets and the radial bearing rotor magnets are axially offset from each other when the pump is at rest.

45. The blood pump recited in claim 44, wherein the offset of the radial bearing stator magnets and the radial bearing rotor magnets is configured to balance with hydrodynamic forces created by pumping action of the impeller.

46. The blood pump recited in claim 44, further comprising front and rear stop points configured to limit an axial range of motion of the rotor relative to the stator in order to maintain the axial offset of the radial bearing stator magnets and the radial bearing rotor magnets.

47. The blood pump recited in claim 46, wherein the stop points are configured to prevent the radial bearing magnets from statically crossing over an unstable magnetic equilibrium point.

48. The blood pump recited in claim 44, wherein a radial motor gap is defined between the between the stator and the rotor, the pump being configured to discharge a primary flow from the fluid outlet over an outside diameter of the housing and being configured to direct a wash flow through the motor gap.

49. The blood pump recited in claim 48, wherein the primary flow is discharged through the fluid outlet at an intermediate angle having both axial and radial components so that the primary flow is directed along an outside surface of the stator assembly that extends the length of the motor stator.

50. The blood pump recited in claim 44, further comprising an outflow sheath for helping to direct the primary flow along the outside of the pump.

51. The blood pump recited in claim 50, wherein the flow produced during operation of the pump expands the sheath to allow the flow to pass through a radial space defined between the pump and the sheath.

52. The blood pump recited in claim 50, wherein the sheath is effective to extend the fluid outlet axially downstream of the fluid inlet.

53. The blood pump recited in claim 50, wherein the sheath is secured to the stator assembly at a location positioned between the fluid inlet and the fluid outlet.

54. The blood pump recited in claim 50, wherein the sheath is constructed such that the fluid inlet and fluid outlet can be placed in a first location with the sheath extending along the outside of the pump and through a lumen into a second location, the sheath forming a conduit for directing pumped blood from the fluid outlet positioned in the first location through the lumen and into the second location.

55. The blood pump recited in claim 50, wherein the sheath is constructed such that the fluid inlet and fluid outlet can be placed in a left ventricle of the heart with the sheath extending along the outside of the pump and through a heart valve into the aorta, the sheath forming a conduit for directing pumped blood from the fluid outlet positioned in the left ventricle through the heart valve and into the aorta.

56. The blood pump recited in claim 50, wherein the sheath is constructed such that the fluid inlet and fluid outlet can be placed in a right ventricle of the heart with the sheath extending along the outside of the pump and through a heart valve into the pulmonary trunk, the sheath forming a conduit for directing pumped blood from the fluid outlet positioned in the right ventricle through the heart valve and into the pulmonary trunk.

57. The blood pump recited in claim 44, wherein the permanent magnet radial bearing stator consists essentially of one or more permanent magnets and the permanent magnet radial bearing rotor consists essentially of one or more permanent magnets.

58. A blood pump comprising:
a stator assembly comprising a motor stator, a fluid inlet, and a fluid outlet;
a rotor assembly comprising a motor rotor and an impeller rotatable about an axis to move fluid from the inlet to the outlet; and
a permanent magnet radial bearing for supporting the rotor assembly for rotation about the axis, the radial bearing comprising:
a permanent magnet radial bearing stator fixed to the stator assembly and a permanent magnet radial bearing rotor fixed to the rotor assembly, the radial bearing being configured such that the radial bearing stator magnets and the radial bearing rotor magnets are axially offset from each other when the pump is at rest, wherein the impeller is configured to produce hydrodynamic forces during pump operation that counteract the net axial pull of the radial bearings which moves the rotor toward the unstable equilibrium condition of the radial bearings so that hydraulic load fluctuations resulting from the natural heartbeat of a patient result in a cyclical oscillation of the rotor relative to the stator.

59. A blood pump comprising:
a housing comprising an elongated tubular side wall that extends along a central axis of the blood pump, the housing having a fluid inlet and a fluid outlet, the fluid outlet comprising at least one opening in the side wall;
an impeller positioned in the housing for rotation about the axis, at least a portion of the impeller being positioned between the fluid inlet and the fluid outlet;
a motor for imparting rotation of the impeller about the axis, the motor comprising:
a stator fixed to the housing;
a rotor coupled to the impeller; and
a permanent magnet radial bearing for supporting the rotor for rotation about the axis, the radial bearing comprising a permanent magnet radial bearing stator and a permanent magnet radial bearing rotor, the radial bearing being configured such that the radial bearing stator magnets and the radial bearing rotor magnets are axially offset from each other when the pump is at rest, wherein the impeller is configured to produce hydrodynamic forces during pump operation that counteract the net axial pull of the radial bearings which moves the rotor toward the unstable equilibrium condition of the radial bearings so that hydraulic load fluctuations resulting from the natural heartbeat of a patient result in a cyclical oscillation of the rotor relative to the stator.

\* \* \* \* \*